US012767636B2

(12) United States Patent
Py et al.

(10) Patent No.: US 12,767,636 B2
(45) Date of Patent: Oct. 20, 2026

(54) PHARMACOLOGICAL CHAPERONE COMPOUNDS OF HUMAN ACID α-GLUCOSIDASE AND THE THERAPEUTIC USE THEREOF

(71) Applicants: UNIVERSITÉ GRENOBLE ALPES, Saint Martin d'Hères (FR); CENTRE NATIONAL DE LA RECHERCHE SCIENTIFIQUE, Paris (FR)

(72) Inventors: Sandrine Py, Saint Martin d'Uriage (FR); Alice Kanazawa, Bernin (FR); Anaïs Vieira Da Cruz, Moirans (FR); Salia Tangara, Lille (FR)

(73) Assignees: UNIVERSITÉ GRENOBLE ALPES, Saint Martin d'Héres (FR); CENTRE NATIONAL DE LA RECHERCHE SCENITFIQUE, Paris (FR)

( * ) Notice: Subject to any disclaimer, the term of this patent is extended or adjusted under 35 U.S.C. 154(b) by 890 days.

(21) Appl. No.: 17/920,297

(22) PCT Filed: Apr. 22, 2021

(86) PCT No.: PCT/EP2021/060572
§ 371 (c)(1),
(2) Date: Oct. 20, 2022

(87) PCT Pub. No.: WO2021/214245
PCT Pub. Date: Oct. 28, 2021

(65) Prior Publication Data

US 2023/0339856 A1 Oct. 26, 2023

(30) Foreign Application Priority Data

Apr. 23, 2020 (FR) ...................................... 2004065

(51) Int. Cl.

| | |
|---|---|
| ***C07D 211/46*** | (2006.01) |
| ***C07D 401/04*** | (2006.01) |
| ***C07D 401/12*** | (2006.01) |
| ***C07D 405/12*** | (2006.01) |
| ***C07D 455/02*** | (2006.01) |
| ***C07D 471/04*** | (2006.01) |

(52) U.S. Cl.
CPC .......... *C07D 211/46* (2013.01); *C07D 401/04* (2013.01); *C07D 401/12* (2013.01); *C07D 405/12* (2013.01); *C07D 455/02* (2013.01); *C07D 471/04* (2013.01)

(58) Field of Classification Search
CPC .. C07D 211/46; C07D 401/04; C07D 401/12; C07D 405/12; C07D 455/02; C07D 471/04
See application file for complete search history.

(56) References Cited

PUBLICATIONS

Boisson, Julien, et al. "Hydroxymethyl-branched polyhydroxylated indolizidines: novel selective α-glucosidase inhibitors." Organic Letters 17.15 (2015): 3662-3665. (Year: 2015).*

International Search Report for PCT/EP2021/060572, mailed Jul. 6, 2021, 3 pages.

Written Opinion of the ISA for PCT/EP2021/060572, mailed Jul. 6, 2021, 5 pages.

Boisson et al., "Hydroxymethyl-Branched Polyhydroxylated Indolizidines: Novel Selective α-Glucosidase Inhibitors", Organic Letters, vol. 17, No. 15, pp. 3662-3665.

Tangara et al., "Aziridination of Cyclic Nitrones Targeting Constrained Iminosugars", Organic Letters, vol. 19, No. 18, pp. 4842-4845.

Vieira Da Cruz et al., "Polyhydroxylated Quinolizidine Iminosugars as Nanomolar Selective Inhibitors of α-Glucosidases", The Journal of Organic Chemistry, vol. 82, No. 18, pp. 9866-9872.

Flanagan et al., "The pharmacological chaperone 1-deoxynojirimycin increases the activity and lysosomal trafficking of multiple mutant forms of acid alpha-glucosidase", Human Mutation, vol. 30, No. 12, pp. 1683-1692.

Ahn et al., "A New Approach to the Synthesis of Monocyclic /8-Lactam Derivatives", J. Org. Chem. 1994, 59, pp. 6282-6286.

Artola et al., "1,6-Cyclophellitol Cyclosulfates: A New Class of Irreversible Glycosidase Inhibitor", American Chemical Society, 2017, pp. 784-793.

Asano et al., "N-Alkylated Nitrogen-in-the-Ring Sugars: Conformational Basis of Inhibition of Glycosidases and HIV-Replication", Journal of Medicinal Chemistry, 1995, 38, pp. 2349-2356.

Bornschein et al., "A Mild and Selective Reduction of β-Lactams: Rh-Catalyzed Hydrosilylation towards Important Pharmacological Building Blocks", 2015, Eur. J. Org. Chem, pp. 1915-1919.

Boyd et al., "Pharmacological Chaperones as Therapeutics for Lysosomal Storage Diseases", 2013, J. Med. Chem. 56, pp. 2705-2725.

Bruckmann et al., "Systematic Structure-Activity Study on Potential Chaperone Lead Compounds for Acid α-Glucosidase", ChemMedChem 2012, 7, pp. 1943-1953.

(Continued)

*Primary Examiner* — Kamal A Saeed
*Assistant Examiner* — Quincy Mckoy
(74) *Attorney, Agent, or Firm* — NIXON & VANDERHYE

(57) ABSTRACT

The invention concerns particular compounds of the imino-sugars class, with a piperidine ring, having a D-gluco configuration and comprising a quaternary centre in the α position of the nitrogen of the piperidine ring. These compounds have the ability to stabilize human acid α-glucosidase while being selective with respect to other glycosidases. They are particularly advantageous for use as chaperone molecules of this enzyme for the treatment of Pompe disease.

14 Claims, 4 Drawing Sheets

(56) References Cited

PUBLICATIONS

D'Alonzo et al., N-Butyl-L-deoxynojirimycin (L-NBDNJ): Synthesis of an Allosteric Enhancer of α-Glucosidase Activity for the Treatment of Pompe Disease, J. Med. Chem, published Nov. 7, 2017, 8 pages.

Khangarot et al., "Kinugasa Reaction: A Direct One-Pot Route to Highly Functionalized β-Lactams", *Eur. J. Org. Chem.* 2013, pp. 7664-7677.

Lahav et al., "A Fluorescence Polarization Activity-Based Protein Profiling Assay in the Discovery of Potent, Selective Inhibitors for Human Nonlysosomal Glucosylceramidase", J. Am. Chem. Soc. 2017, 139, pp. 14192-14197.

Markham, "Migalastat: First Global Approval", 2016, Drugs 76. pp. 1147-1152.

Niesen et al., "The use of differential scanning fluorimetry to detect ligand interactions that promote protein stability", Nature Protocols, vol. 2, No. 9, 10 pages.

Parenti et al., "Pharmacological Enhancement of Mutated α-Glucosidase Activity in Fibroblasts from Patients with Pompe Disease", 2007, Mol. Ther. vol. 15, No. 3, pp. 508-514.

Porto et al., "Pharmacological Enhancement of—α Glucosidase by the Allosteric Chaperone N-acetylcysteine", Molecular Therapy vol. 20 No. 12, 2201-2211 Dec. 2012, 11 pages.

Stecko et al., "Kinugasa reaction: an 'ugly duckling' of b-lactam chemistry", Tetrahedron 70 (2014) pp. 7817-7844.

Wennekes et al., "Dual-Action Lipophilic Iminosugar Improves Glycemic Control in Obese Rodents by Reduction of Visceral Glycosphingolipids and Buffering of Carbohydrate Assimilation", J. Med. Chem. 2010, 53, pp. 689-698.

Xie et al., "Tertiary amine synthesis via reductive coupling of amides with Grignard reagents", 2017, Chem. Sci. 8. pp. 7492-7497.

* cited by examiner

III V A-1 I'a (R$^1$ = H)
IIc (R$^8$ = Ph)

III B-2 C-2

D-2 IId
(I'a with R$^1$ = H, R$^8$ = OH)

III VI A-3 I'd (R$^1$ = H )

III
VII
A-4
IIa: $R^8$ = H
IIb: $R^8$ = $CH_3$
D-4
IIa: $R^8$ = H
IIb: $R^8$ = $CH_3$
IIe: $R^1$ = *n*-Pr, $R^8$ = H
from E-4b
E-4
E-4a: $R^1$ = $R^{17}$ = allyl
E-4b: $R^1$ = allyl, $R^{17}$ = vinyl
Ia
F-4a: n = 1 from E-4a
F-4b: n = 0 from E-4b
IIf: n = 1
IIg: n = 0

PHARMACOLOGICAL CHAPERONE COMPOUNDS OF HUMAN ACID α-GLUCOSIDASE AND THE THERAPEUTIC USE THEREOF

CROSS-REFERENCE TO RELATED APPLICATIONS

This application is the U.S. national phase of International Application No. PCT/EP2021/060572 filed Apr. 22, 2021, which designated the U.S. and claims priority to FR Patent Application No. 2004065 filed Apr. 23, 2020, the entire contents of each of which are hereby incorporated by reference.

BACKGROUND OF THE INVENTION

Field of the Invention

The present invention lies in the field of the treatment of lysosomal diseases, more specifically the treatment of Pompe disease.

More particularly, the present invention relates to compounds, belonging to the class of iminosugars, capable of selectively interacting with human α-glucosidases and in particular of stabilizing human acid α-glucosidase in its endogenous form (GAA) or of recombinant nature (rhGAA), in a conformation favoring transport thereof to the lysosome, for use thereof as a drug, in particular for treating Pompe disease; and to a pharmaceutical composition containing such compounds. The invention also relates to compounds belonging to the class of iminosugars capable of selectively interacting with human acid α-glucosidase. The invention furthermore relates to a method for preparing such compounds.

Description of the Related Art

Pompe disease, or type 2 glycogenosis, is a rare genetic disease characterized by one or more mutations of the GAA gene encoding the human acid α-glucosidase (GAA) lysosomal enzyme, which causes a deficit in the activity of this enzyme, and consequently the accumulation of glycogen, the hydrolytic biodegradation of which is performed by this enzyme, in the lysosomes, which causes cell malfunctionings in the muscles and heart. The symptoms are diverse, and progression thereof more or less rapid depending on whether the disease manifests at birth or at an adult age. They affect all the muscles, in particular the respiratory muscles and the myocardium. The life expectation of the subjects affected is reduced thereby, especially in babies, who die in the course of their first year of life.

At the present time there is only one treatment for Pompe disease that has received authorization for marketing. This treatment, known as enzyme replacement therapy (ERT), consists in intravenously administering the Myozyme® specialty, the active principle of which is a recombinant human acid α-glucosidase (rhGAA), which makes it possible to stabilize the symptoms of the disease. However, this treatment has numerous drawbacks: it is very expensive, binding for the patient, since it requires perfusion every two weeks, in a hospital environment, and it is of limited efficiency in many cases. It may indeed cause an immune reaction affecting its efficiency and its tolerance by the subject being treated. Furthermore, the recombinant enzyme is relatively unstable in the blood, and the doses that have to be administered to the patients are much greater than those administered for treating other lysosomal diseases.

There thus remains at the present time a need for a satisfactory treatment of Pompe disease.

SUMMARY OF THE INVENTION

The present invention aims to propose such a treatment. More particularly, the invention aims to propose compounds affording effective treatment of Pompe disease, this treatment furthermore being easy to administer, and less expensive than the treatment by enzyme replacement therapy proposed by the prior art. An additional objective of the invention is that these compounds, administered at the same time as the enzyme replacement therapy treatment of the prior art, significantly increase the efficiency of the latter.

Seeking to achieve these objectives, the present inventors became interested in a therapeutic approach considered at the present time to be one of the most promising for treating lysosomal diseases: the use of so-called pharmacological chaperone molecules. Chaperone molecules are small molecules promoting the correct folding of mutant enzymes and enabling transport thereof to the lysosomes (Boyd et al., 2013, J. Med. Chem. 56: 2705-2725) rather than degradation at the endoplasmic reticulum. This therapeutic approach was implemented successfully for another lysosomal disease, Fabry disease, against which the migalastat iminosugar (Galafold®) is now prescribed as a pharmacological chaperone of acid α-galactosidase (Markham, 2016, Drugs 76: 1147-1152).

The present inventors have thus sought compounds capable of stabilizing human acid α-glucosidase in its active folded form, as well as increasing the efficacy of the recombinant human acid α-glucosidase used in treatments by enzyme replacement therapy, in order to use them in the treatment of Pompe disease.

Among the existing compounds, deoxynojirimycin (DNJ), an iminosugar of formula:

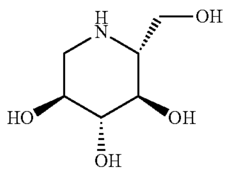 [SMILES: OC[C@H]1NC[C@H](O)[C@@H](O)[C@@H]1O]

has been proposed by the prior art as potential chaperone molecule of human acid α-glucosidase (Flanagan et al., 2009, Hum. Mutat. 30: 1683-1692).

A derivative of DNJ, called NB-DNJ, of formula:

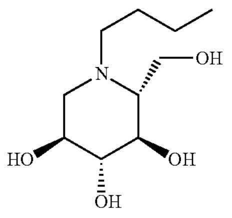

has also been proposed by the prior art for the same application (Parenti et al., 2007, Mol. Ther. 15(3): 508-14).

However, these compounds have low selectivity for this enzyme, and they inhibit other human enzymes, both of α- and β-glycosidase type, and glycosyltransferases, which causes many undesirable side effects when they are administered to a subject.

The publication by Boisson et al., Org. Lett., 2015, 17(15), 3662-5 describes particular polyhydroxylated derivatives of indolizidines having good ability to inhibit an α-glucosidase of *S. cerevisiae* and a rice α-glucosidase.

The publication by Tangara et al., Org. Lett., 2017, 19(18), 4842-5, describes particular aziridinyl-iminosugars.

The publication by Vieira Da Cruz et al., J. Org. Chem., 2017, 82(18), 9866-72 describes particular polyhydroxylated quinolizidines and their ability to inhibit yeast and rice α-glucosidases.

The present inventors have now discovered that specific compounds, belonging to the iminosugars class, complying with a particular structure derived from that of DNJ, bind to human acid α-glucosidase (GAA) and stabilize it, and this in a highly selective manner, i.e. without interacting, at least significantly, with other human glycosidases, in particular with human β-glucocerebrosidases (GBA1 and GBA2), human β-glucosylceramide transferase (GCS) or with the human endoplasmic reticulum α-glucosidase II (GANAB). The effect of stabilizing GAA by these compounds is furthermore particularly great. Thus, administered to patients suffering from Pompe disease, these compounds make it possible to stabilize their endogenous acid α-glucosidase in a correctly folded form to improve transport thereof to the lysosomes and to increase its activity of hydrolysis of glycogen, and therefore to effectively treat this disease, while reducing undesirable side effects during treatment. These compounds also make it possible, associated with enzyme replacement therapy (ERT), to stabilize the recombinant enzyme (rhGAA), thereby increasing the efficacy thereof.

Molecules with a similar, but different, structure, such as DNJ or NB-DNJ, do not make it possible to obtain such a particularly advantageous result on a therapeutic level.

Thus, according to a first aspect, the present invention relates to a compound of general formula (I) below, or one of the pharmaceutically acceptable salts thereof, for use as a drug, in particular as a pharmacological chaperone, in particular for treating Pompe disease, in particular for stabilizing human acid α-glucosidase:

(I)

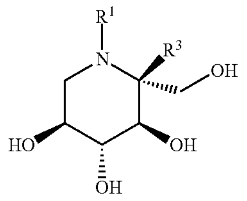

wherein:

$R^1$ represents a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, and $R^2$ represents a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, said hydrocarbon radical comprising at least 2 carbon atoms when $R^1$ represents a hydrogen atom, or $R^1$ and $R^2$ form together, with the atoms of the piperidine ring to which each is attached, a 3- to 6-membered heterocycle fused with the piperidine ring, optionally substituted by one or more radicals, which may be identical or different, each selected from a hydroxyl group, an amino group or a carbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused. Such a configuration encompasses the cases wherein the carbon radical is branched to the 3- to 6-membered heterocycle by a carbon atom, as well as the cases wherein the carbon radical is branched thereto by means of a heteroatom that it includes.

The term heteroatom designates, in the present description, conventionally per se, any atom belonging to an element other than carbon and hydrogen, such as a nitrogen, oxygen, sulfur, phosphorus, silicon, halogen, etc. atom.

Preferentially, when $R^1$ represents a hydrogen atom, $R^2$ does not represent a methyl radical or a benzyl group.

In the present description, "pharmaceutically acceptable salt", conventionally per se, means any salt of the compound of general formula (I) comprising, as a counter-ion, a substance that does not produce any adverse, allergic or otherwise undesirable reaction when it is administered to a subject, in particular to a mammal.

Any conventional pharmaceutically acceptable salt of the compound of general formula (I) can be used according to the invention. By way of examples, mention can be made of chlorides, bromides, formiates, acetates, etc.

In the present description, the term "treatment" means the obtaining of a desired pharmacological or physiological effect. The word "treatment", as used in the present description, comprises the prevention or the partial prevention of one or more of the symptoms of the disease and/or the partial or total curing of the disease and/or the total or partial disappearance of one or more of the symptoms thereof.

Human acid α-glucosidase is a protein of 952 amino acids, of GenBank Accession No. AB153718.1.

The compound used according to the invention, having the general formula (I), is a ligand thereof. It furthermore has particularly strong selectivity with respect to this enzyme. This selectivity is in particular much greater than that of DNJ or NB-DNJ, or other iminosugars interacting with glycosidases.

The characteristics of the compound used according to the invention, relating in particular to the three-dimensional structure thereof, which make it possible to obtain such advantageous properties, will not be prejudged here. It can however be supposed that the following participate therein: the presence of a quaternary center in the a position with respect to the nitrogen of the piperidine nucleus, the D-gluco configuration of the compound, and the particular substituents present on the quaternary carbon in the a position with respect to the nitrogen of the piperidine nucleus and on this nitrogen. Because, at least partly, of these characteristics, the compounds used according to the invention would bind non-covalently with the enzyme and would stabilize the folding thereof, conferring on it a role of chaperone making it possible to restore the transport and the activity of the deficient enzyme in the lysosomes.

The compound used according to the invention thus stabilizes the human acid α-glucosidase at low concentrations, and it has the essential properties of pharmacological chaperones suitable for treating Pompe disease. In particular, at a concentration of 100 μM, it increases, in vitro, the thermal denaturing temperature of the human acid α-glucosidase from 8 to 12° C. at pH 4.0 and the thermal denaturing temperature of the human acid α-glucosidase from 10 to 13° C. at pH 7.4. The chaperone effect of the compound used according to the invention on human acid α-glucosidase is confirmed by experiments on human cells in culture, more precisely fibroblasts of patients suffering from the disease, as well as, in vivo, in mice.

The compound used according to the invention is therefore entirely adapted and advantageous for being used as a pharmacological chaperone for treating Pompe disease, by selective bonding to the human acid α-glucosidase and stabilization thereof, thus restoring the activity of the deficient enzyme of the patient, and/or improving the bioavailability of the rhGAA recombinant enzyme administered during rhGAA enzyme replacement therapy when this therapy is associated with use of the compound used according to the invention.

Thus the compound of general formula (I) can be used for stabilizing human acid α-glucosidase in its active folded form, as well as increasing the efficacy of the recombinant human acid α-glucosidase used in enzyme replacement therapy treatments, the compound of general formula (I) and the recombinant human acid α-glucosidase being co-administered to the patient.

The compound used according to the invention can advantageously be administered to the patient easily, in particular orally, and it is inexpensive to prepare.

It has a low risk of toxicity, and good bioavailability.

Furthermore, in association with enzyme replacement therapy, the compound used according to the invention advantageously improves the bioavailability of the recombinant enzyme injected, which makes it possible to reduce the doses thereof to obtain a same efficacy in treatment, and even superior efficacy.

The compound used according to the invention, of general formula (I), can be administered to any subject in need thereof, i.e. suffering from or likely to contract the disease. This subject may in particular be a mammal, and especially a human.

The compound used according to the invention is preferably administered to the subject in a therapeutically effective amount.

"Therapeutically effective amount" means an amount of the compound which, when it is administered to a subject to treat the disease, is sufficient to ensure such treatment of the disease.

The therapeutically effective amount of the compound used according to the invention depends on several factors, such as the disease and its seriousness, the age, the weight, etc. of the subject to be treated, the particular compound used, the route and form of administration, etc. The therapeutically effective amount of the compound used according to the invention will be determined by the doctor for each individual case.

The compound used according to the invention can be administered to the subject to be treated by any method conventional per se, in particular parenterally, for example subcutaneously, subdurally, intravenously, by intramuscular, intrathecal, intraperitoneal, intracerebral, intra-arterial or intralesion route; intranasally; rectally; by pulmonary route, for example by aerosol or inhalation, or even topically. It is preferentially administered orally. Determining the administration posology of the compound used according to the invention falls within the competence of a doctor. The compound can for example be administered to the subject in need thereof once or twice per day, over a long period, at regular intervals, or in a targeted manner during an associated treatment by enzyme replacement therapy.

As disclosed above, the compound used according to the invention can advantageously be administered to the subject conjointly with an enzyme used for enzyme replacement therapy, in particular conjointly with a recombinant human acid α-glucosidase such as the recombinant enzyme sold under the name Myozyme®. It then advantageously increases the efficacy thereof.

In particular embodiments of the invention, in the general formula (I) $R^1$ and $R^2$ are independent from each other, in the sense that they are not bonded to each other, in particular that they do not form together a ring fused with the piperidine nucleus of the compound.

In particular, in the general formula (I):

$R^1$ then represents a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, and $R^2$ can represent a —CH($R^3$)—$R^4$ group, wherein $R^3$ and $R^4$, which may be identical or different, each represent a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^3$ and $R^4$ not simultaneously representing a hydrogen atom when $R^1$ represents a hydrogen atom.

In particular embodiments of the invention, $R^3$ and $R^4$ do not simultaneously represent a hydrogen atom.

In particular embodiments of the invention, $R^1$ and $R^2$ are such that they do not simultaneously represent, respectively, a propyl radical and an ethyl radical. Preferentially, $R^3$ and $R^4$ are such that, when $R^1$ and $R^3$ each represent a hydrogen atom, $R^4$ does not represent a phenyl radical.

In particular embodiments of the invention, $R^2$ represents a —CH($R^3$)—$R^4$ group, wherein $R^3$ is as defined above and $R^4$ represents a hydrocarbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising a single ring or a plurality of rings, optionally fused, and comprising one or more heteroatoms each selected from oxygen, nitrogen, sulfur and silicon and/or one or more groups including at least one heteroatom each selected from the carbonyl, sulf oxide, sulfonyl and silane groups.

Otherwise, $R^1$ representing a hydrogen atom or a hydrocarbon radical, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused, $R^2$ may represent a $—(CHR^7)—SO_2—Ar^1$ group wherein $Ar^1$ represents an aryl or heteroaryl radical, optionally substituted, comprising in particular from 5 to 18 atoms, and $R^7$ represents a hydrogen atom or a hydrocarbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused. In particular embodiments of the invention, $Ar^1$ represents an aromatic heterocycle, in particular a pyridine ring, optionally substituted, and/or $R^7$ represents a hydrogen atom.

In particular embodiments of the invention, $R^1$ representing a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^2$ may represent a triazole group, optionally substituted.

In other variants of the invention, $R^1$ representing a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^2$ represents a $—(CH_2)_2—R^8$ group, wherein $R^8$ represents:

- a hydrogen atom;
- a C1-C12 alkyl or cycloalkyl group, optionally comprising a single ring or a plurality of fused rings, such as an adamantyl group for example;
- a $—(CH_2)_a—OH$ group wherein a is an integer between 0 and 18, preferably between 0 and 12 and in particular between 0 and 6;
- a $—(CH_2)_b—Ar_2$ group wherein $Ar^2$ represents an aryl or heteroaryl radical, optionally substituted, optionally comprising one or more heteroatoms and/or one or more groups including at least one heteroatom and optionally comprising a single ring or a plurality of rings optionally fused, and b is an integer between 0 and 18, preferably between 0 and 12 and in particular between 0 and 6;
- a $—(CH_2)_c—Si(R^9)_3$ group wherein $R^9$ represents a hydroxyl radical, a C1-C4 alkyl radical, a C1-C4 alkoxyl radical or a phenyl radical, and c is an integer between 0 and 18, preferably between 0 and 12 and in particular between 0 and 6;
- or a $—(CH_2)_d—Z—R^{10}$ group wherein Z is a heteroatom selected from oxygen, nitrogen and sulfur, $R^{10}$ represents a hydrogen atom or a C1-C18, preferably C1-C12 and in particular C1-C6, alkyl, cycloalkyl, alkylaryl, aryl or acyl radical, said radical optionally being interrupted and/or substituted by one or more heteroatoms and/or one or more groups including at least one heteroatom, in particular a sulfonyl radical, and d is an integer between 0 and 18, preferably between 0 and 12 and in particular between 0 and 6.

In particularly preferred embodiments of the invention, $R^1$ represents a hydrogen atom or a C1-C18, preferably C1-C6, for example C1-C3 and more particularly C1-C2, linear, branched and/or cyclic alkyl group, this alkyl group optionally being interrupted and/or substituted by one or more heteroatoms and/or one or more groups including at least one heteroatom.

The compound used according to the invention can in particular comply with the general formula (I'a):

(I'a)

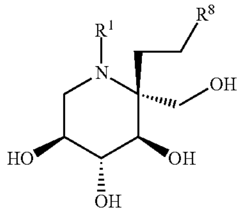

wherein:

$R^1$ represents a hydrogen atom or C1-C18, preferably C1-C6, linear, branched and/or cyclic alkyl group, optionally interrupted and/or substituted by one or more heteroatoms and/or one or more groups including at least one heteroatom, and $R^8$ represents:

- a hydrogen atom;
- a methyl, ethyl, propyl, butyl, pentyl, hexyl, cycloalkyl, adamantyl, alkylcycloalkyl, alkylaryl or aryl radical, in particular phenyl radical, said radical optionally being interrupted and/or substituted by one or more heteroatoms and/or one or more groups including at least one heteroatom;
- a hydroxyl group;
- a $—Si(R^{12})_3$ group wherein $R^{12}$ represents a hydroxyl radical, a C1-C4 alkyl radical, a C1-C4 alkoxyl radical or a phenyl radical;
- a $—(CH_2)_f—Y—R^{13}$ group wherein f is an integer between 0 and 6, Y is a heteroatom selected from oxygen, nitrogen and sulfur and $R^{13}$ represents a C1-C18, preferably C1-C12 and in particular C1-C6, alkyl radical, or a C1-C18, preferably C1-C12 and in particular C1-C6, aryl or heteroaryl radical;
- a $—(CH_2)_g—CO—R^{13}$ group wherein g is an integer between 0 and 6 and $R^{13}$ is as defined above;
- or a $—(CH_2)_h—SO_e—R^{13}$ group wherein h is an integer between 0 and 6, e is equal to 1 or 2 and $R^{13}$ is as defined above, $R^8$ not representing a hydrogen atom when $R^1$ represents a propyl radical.

In particular embodiments of the invention, the compound used complies with the general formula (I"a):

(I"a)

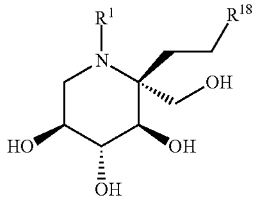

wherein:

$R^1$ represents a hydrogen atom or a C1-C18 linear, branched and/or cyclic alkyl group, optionally interrupted and/or substituted by one or more heteroatoms and/or one or more groups including at least one heteroatom, $R^{18}$ represents a linear, branched and/or cyclic hydrocarbon radical, saturated or unsaturated, aromatic or not, optionally substituted, comprising 4 to 18 carbon atoms, preferably 4 to 12 carbon atoms, and in particular 5 to 12 carbon atoms, optionally comprising one or more heteroatoms and/or one or more groups including at least one heteroatom and optionally comprising a single ring or a plurality of rings optionally fused.

$R^{18}$ may in particular represent a butyl, pentyl, hexyl, cyclohexyl, phenyl, benzyl or adamantyl group.

Preferentially, in formula (I"a), $R^1$ represents a hydrogen atom.

Particular compounds that can be used according to the invention comply with the following formulae (IIa), (IIb), (IIb1), (IIb2), (IIb3), (IIb4), (IIb5), (IIb6), (IIb7), (IIc), (IIc1), (IId), (IIe), (IIo), (IIp), (IIp1), (IIq), (IIr), (IIs), (IIt), (IIu), (IIv), (IIw), (IIw1), (IIx), (IIx1), and (IIy):

(IIa)

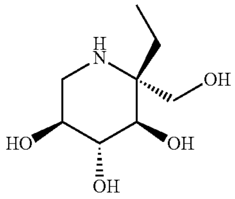

(IIb)

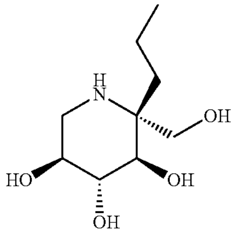

(IIb1)

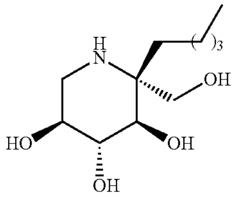

(IIb2)

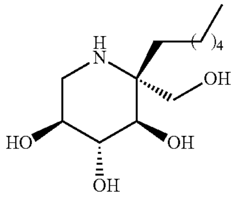

(IIb3)

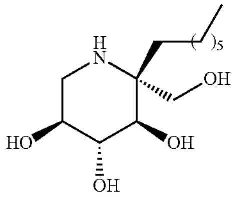

-continued (IIb4)

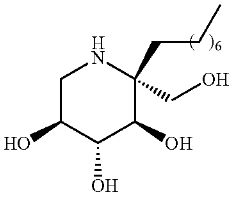

(IIb5)

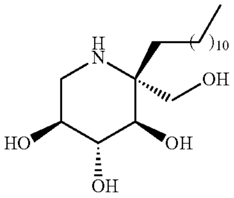

(IIb6)

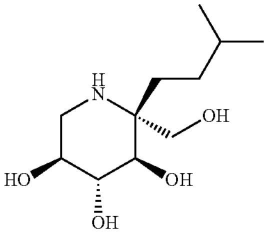

(IIb7)

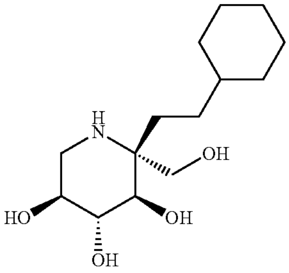

(IIc)

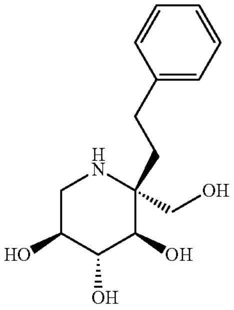

(IIc1)

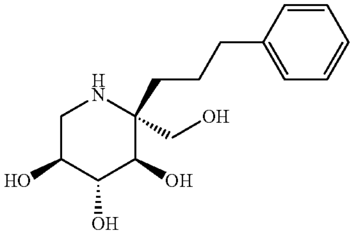

-continued
(IId)
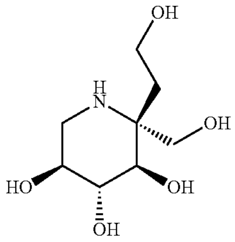
(IIe)
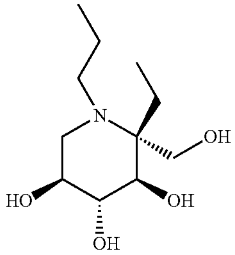
(IIo)
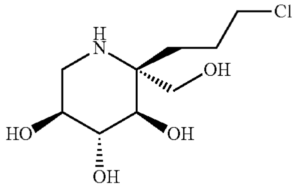
(IIp)
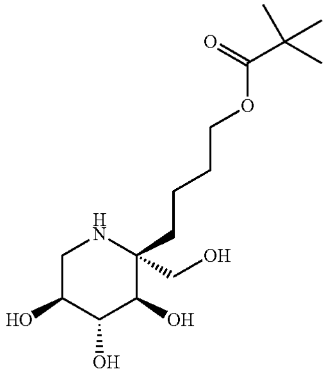
(IIp1)
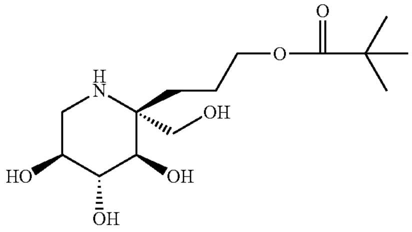
(IIq)
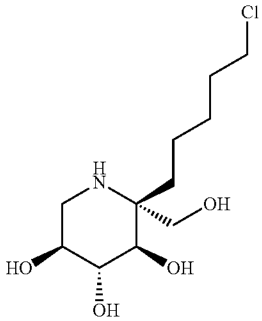
-continued
(IIr)
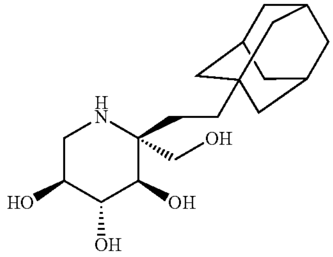
(IIs)
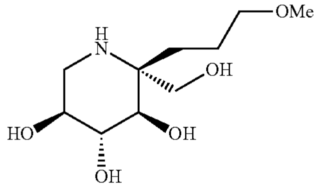
(IIt)
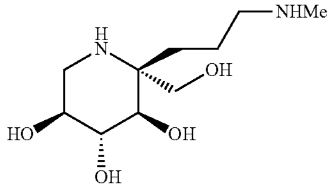
(IIu)
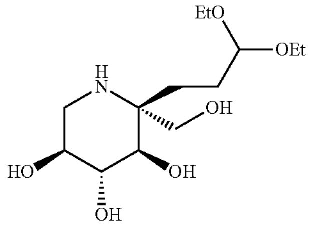
(IIv)
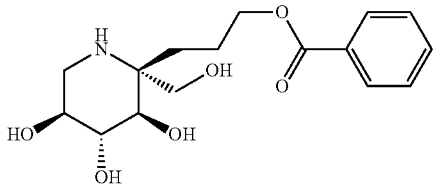
(IIw)
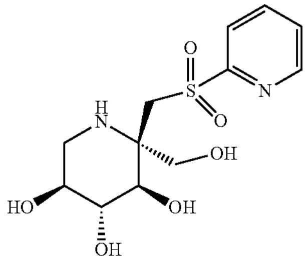
(IIw1)
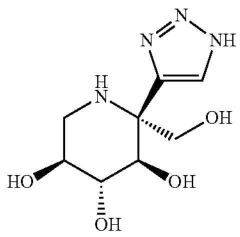

-continued (IIx)

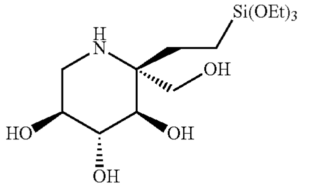

(IIx1)

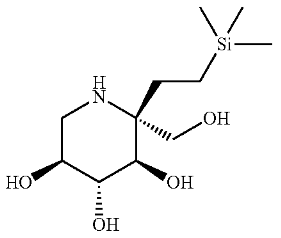

(IIy)

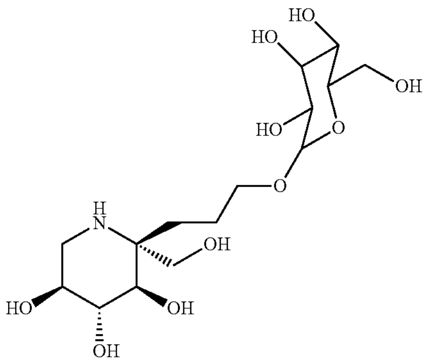

In alternative embodiments of the invention, the compound used is such that, in the general formula (I), $R^1$ and $R^2$ form together, with the atoms of the piperidine ring to which each is attached, a 6-membered heterocycle fused with the piperidine ring, optionally substituted by one or more radicals, which may be identical or different, each selected from a hydroxyl group, an amino group, a carbonyl group or a carbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused.

A particular compound that can be used according to the invention complies with the formula (IIf):

(IIf)

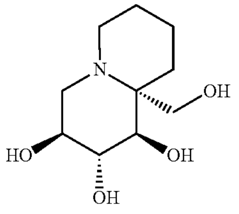

In other embodiments of the invention, the compound used is such that, in the general formula (I), $R^1$ and $R^2$ form together, with the atoms of the piperidine ring to which each is attached, a 5-membered heterocycle fused with the piperidine ring, optionally substituted by one or more radicals, which may be identical or different, each selected from a hydroxyl group, an amino group, a carbonyl group or a carbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused.

A particular compound that can be used according to the invention complies with the formula (IIg):

(IIg)

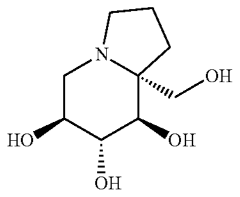

In further alternative embodiments of the invention, the compound used is such that, in the general formula (I), $R^1$ and $R^2$ form together, with the atoms of the piperidine ring to which each is attached, a 4-membered heterocycle fused with the piperidine ring, optionally substituted by one or more radicals, which may be identical or different, each selected from a hydroxyl group, an amino group or a carbon radical, preferably including from 1 to 18, preferentially from 1 to 12 and in particular from 1 to 6, carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused.

The compound may in particular comply with the general formula (I'b):

(I'b)

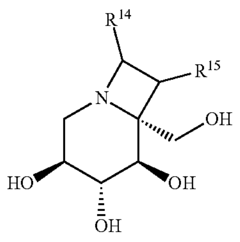

wherein $R^{14}$ represents a hydrogen atom, a carbonyl radical or a C1-C18, preferably C1-C12 and in particular C1-C16, alkyl, alkenyl, alkynyl, alkylaryl or aryl radical, said radical optionally being interrupted and/or substituted by one or more heteroatoms and/or one or more groups including at least one heteroatom, and $R^{15}$ represents a hydrogen atom, a hydroxyl radical, an amino radical, or a C1-C18, preferably C1-C12 and in particular C1-C6, alkyl, alkenyl or aryl radical, said radical optionally being interrupted and/or substituted by one or more heteroatoms and/or one or more groups including at least one heteroatom. Particular compounds that can be used according to the invention comply in particular with the formulae (IIh), (IIz1), (IIz2), (IIz3), (IIz4), and (IIz5):

(IIh)

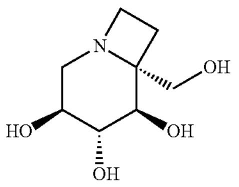

(IIz1)

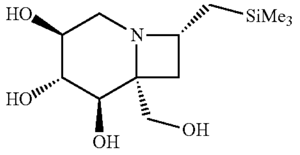

(IIz2)

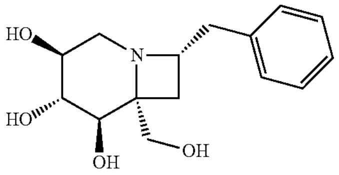

(IIz3)

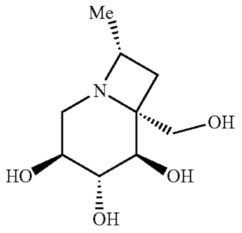

(IIz4)

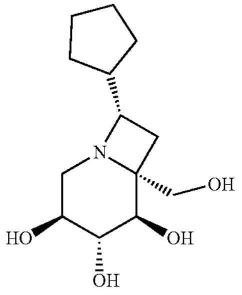

(IIz5)

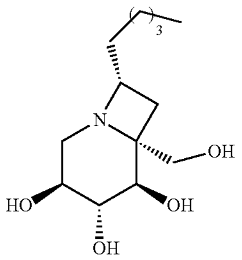

In still alternative embodiments of the invention, the compound used is such that, in the general formula (I), $R^1$ and $R^2$ form together, with the atoms of the piperidine ring to which each is attached, a 3-membered heterocycle fused with the piperidine ring, optionally substituted by a —X—$R^5$ group, wherein:

X represents a —C(═O)— or —CH($OR^6$)— radical wherein $R^6$ represents a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, and $R^5$ represents a hydrogen atom, an amino group, or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, or X represents a —CH(OH)— radical and $R^5$ represents a hydrogen atom, or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused. In the latter configuration, in particular, $R^5$ preferentially does not represent a non-substituted n-propyl radical, a non-substituted c-hexyl radical or a non-substituted phenyl radical.

The compound used according to the invention may in particular comply with the general formula (I'c):

(I'c)

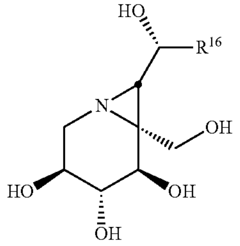

wherein $R^{16}$ represents a hydrogen atom or a C1-C18, preferably C1-C12 and preferentially C1-C6, alkyl radical, said radical optionally being interrupted and/or substituted by one or more heteroatoms and/or one or more groups including at least one heteroatom.

In particular, $R^{16}$ may represent a —$CH_2$—OH group, a methyl radical or an ethyl radical.

Particular compounds that can be used according to the invention comply with the formulae (IIj), (IIk), (IIm) and (IIn):

(IIj)

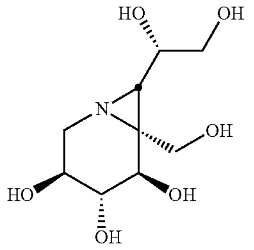

-continued (IIk)

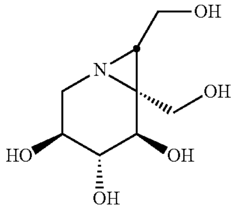

(IIm)

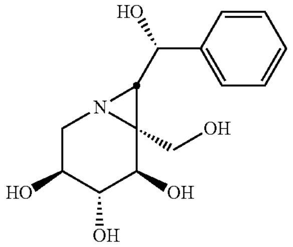

(IIn)

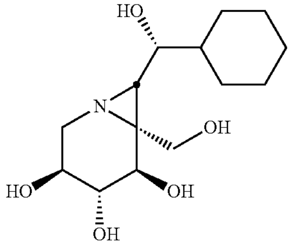

The invention can also be expressed in the terms of a method for the therapeutic treatment of a subject suffering from or likely to contract a disease, in particular Pompe disease, this method comprising a step of administering to said subject in need thereof a therapeutically effective amount of a compound complying with the general formula (I) or one of the pharmaceutically acceptable salts thereof. This method may comply with one or more of the features described above in reference to the therapeutic use of the compound of general formula (I), or one of the pharmaceutically acceptable salts thereof, as a drug.

The invention also relates to the use of a compound of general formula (I), or one of the pharmaceutically acceptable salts thereof, as defined above, for manufacturing a drug, in particular a drug for treating Pompe disease.

According to another aspect, the present invention relates to a pharmaceutical composition containing, as active principle, a compound complying with the general formula (I) or one of the pharmaceutically acceptable salts thereof, in a pharmaceutically acceptable vehicle.

In the present description, "pharmaceutically acceptable vehicle" means any vehicle useful for preparing a pharmaceutical composition and which is generally safe, non-toxic and neither biologically nor otherwise undesirable for the subject to be treated, in particular for mammals and especially humans. The vehicle of the pharmaceutical composition according to the invention may be either solid or semi-solid or liquid. It may be a diluent, an adjuvant or any other vehicle conventional in itself for forming pharmaceutical compositions.

The pharmaceutical composition according to the invention may be in any galenic form, in particular in a form adapted to administration parenterally, intranasally, rectally, or by pulmonary or topical route. Preferentially, it is in a form suitable for oral administration. By way of examples of such galenic forms, non-limitative of the invention, mention can be made of the forms of granules, powder, tablets, capsules, pills, syrup, solution or drinkable suspension, etc. The pharmaceutical composition according to the invention may contain one or more excipients/additives conventional in themselves for forming pharmaceutical compositions, for example selected from preservatives, sweeteners, flavorings, fillers, disintegrators, wetting agents, emulsifiers, surfactants, dispersants, lubricants, stabilizers, buffers, antibacterial agents, antifungal agents, etc., or any one of the mixtures thereof; and/or any compound allowing rapid, prolonged or delayed, and/or targeted, release of the active principle after administration thereof to the subject.

The pharmaceutical composition according to the invention may furthermore contain one or more active principles other than the compound of general formula (I) or one of the pharmaceutically acceptable salts thereof, these active principles being able or not to act synergically with said compound.

The pharmaceutical composition according to the invention is preferably formulated in the form of unit doses.

The invention also relates to the therapeutic use of a pharmaceutical composition according to the invention, as defined above, for treating a disease, in particular Pompe disease. This use may comply with one or more of the features described above in reference to the therapeutic use of the compound of general formula (I) or of one of the pharmaceutically acceptable salts thereof.

According to another aspect, the present invention relates to a compound complying with the following general formula (I'), this general formula (I') defining a subfamily of the compounds of general formula (I) described above, or one of the pharmaceutically acceptable salts thereof:

(I')

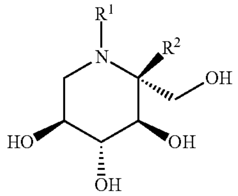

wherein:

$R^1$ represents a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, and $R^2$ represents a —CH($R^3$)—$R^4$ group, wherein $R^3$ and $R^4$, which may be identical or different, each represent a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^3$ and $R^4$ being such that, when $R^1$ and $R^3$ each represent a hydrogen atom, $R^4$ does not represent a hydrogen atom or a phenyl radical, and $R^1$ and $R^2$ being such that they do not simultaneously represent respectively a propyl radical and an ethyl radical, or $R^1$ and $R^2$ form together, with the atoms of the piperidine ring to which each is attached, a 4-membered heterocycle fused with the piperidine ring, optionally substituted by one or more radicals, which may be identical or different, each selected from a hydroxyl group, an amino group or a carbon radical, preferably comprising from 1 to 18, preferentially from 1 to 12 and in particular from 1 to 6 carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused, or $R^1$ and $R^2$ form together, with the atoms of the piperidine ring to which each is attached, a 3-membered heterocycle fused with the piperidine ring, optionally substituted by a —X—$R^5$ group, wherein:

X represents a —C(═O)— or —CH($OR^6$)— radical wherein $R^6$ represents a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, and $R^5$ represents a hydrogen atom, an amino group or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused;

or X represents a —CH(OH)— radical and $R^5$ represents a hydrogen atom or a hydrocarbon radical, for example comprising from 1 to 6 carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused, $R^5$ not representing an n-propyl radical, a c-hexyl radical or a phenyl radical. Here n-propyl radical, c-hexyl radical and phenyl radical mean these radicals in non-substituted form. Thus, $R^5$ may represent a substituted n-propyl radical, a substituted c-hexyl radical or a substituted phenyl radical.

In particular embodiments of the invention, the compound is such that, in the formula (I'):

$R^1$ represents a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, and $R^2$ represents a —CH($R^3$)—$R^4$ group, wherein $R^3$ is as defined above and $R^4$ represents a hydrocarbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising a single ring or a plurality of rings, optionally fused, and including one or more heteroatoms each selected from oxygen, nitrogen, sulfur and silicon and/or one or more groups including at least one heteroatom each selected from the carbonyl, sulfoxide, sulfonyl and silane groups; $R^4$ not representing a phenyl radical when $R^1$ and $R^3$ each represent a hydrogen atom.

In particular, in the formula (I'), when $R^1$ represents a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^2$ may represent a —($CHR^7$)—$SO_2$—$Ar^1$ group wherein $Ar^1$ represents an aryl or heteroaryl radical, optionally substituted, preferably comprising from 5 to 18 atoms, and $R^7$ represents a hydrogen atom or a hydrocarbon radical, preferably comprising from 1 to 18, preferentially from 1 to 12 and in particular from 1 to 6, carbon atoms, linear, branched and/or cyclic, saturated or unsaturated, aromatic or not, optionally substituted, optionally comprising one or more heteroatoms and/or one or more groups including at least one heteroatom and optionally comprising a single ring or a plurality of rings optionally fused.

The compound according to the invention may for example comply with the general formula (I'd):

(I'd)

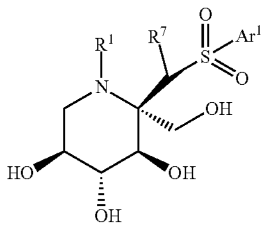

wherein $R^1$, $R^7$ and $Ar^1$ are as defined above.

Otherwise, in the formula (I'), when $R^1$ represents a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^2$ may represent a triazole group, optionally substituted.

The compound according to the invention may in particular comply with the formula (I'e):

(I'e)

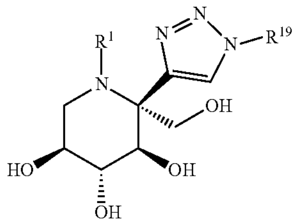

wherein $R^1$ is as defined above and $R^{19}$ represents a hydrogen atom or a C1-C18 alkyl, alkylaryl, trialkylsilyl or aryl radical, said radical optionally being interrupted and/or substituted by one or more heteroatoms and/or one or more groups including at least one heteroatom.

In variants of the invention, in the general formula (I'), $R^1$ representing a hydrogen atom or a linear, branched and/or cyclic hydrocarbon radical, saturated or unsaturated, aromatic or not, optionally substituted, optionally comprising one or more heteroatoms and/or one or more groups including at least one heteroatom and optionally comprising a single ring or a plurality of rings optionally fused, $R^2$ represents a $-(CH_2)_2-R^8$ group, wherein $R^8$ represents:

a hydrogen atom;

a C1-C12 alkyl or cycloalkyl group, optionally substituted, optionally comprising a single ring or a plurality of fused rings, such as an adamantyl radical;

a $-(CH_2)_a-OH$ group wherein a is an integer between 0 and 18, preferentially between 0 and 12 and in particular between 0 and 6; optionally, a may be different from 1 when $R^1$ represents a hydrogen atom;

a $-(CH_2)_b-Ar^2$ group wherein $Ar^2$ represents an aryl or heteroaryl radical, optionally substituted, optionally comprising one or more heteroatoms and/or one or more groups including at least one heteroatom and optionally comprising a single ring or a plurality of rings optionally fused, and b is an integer between 0 and 18, preferentially between 0 and 12 and in particular between 0 and 6; optionally, b may be different from 1 when $R^1$ represents a hydrogen atom and $Ar^2$ represents a phenyl radical;

a $-(CH_2)_b-Si(R^9)_3$ group wherein $R^9$ represents a hydroxyl radical, a C1-C4 alkyl radical, a C1-04 alkoxyl radical or a phenyl radical and c is an integer between 0 and 18, preferentially between 0 and 12 and in particular between 0 and 6;

or a $-(CH_{hd\ 2})_d-Z-R^{10}$ group wherein Z is a heteroatom selected from oxygen, nitrogen and sulfur, $R^{19}$ represents a C1-C18, preferably C1-C12 and in particular C1-C6, alkyl, cycloalkyl, alkylaryl, aryl or acyl radical, said radical optionally being interrupted and/or substituted by one or more heteroatoms and/or one or more groups including at least one heteroatom, such as a sulfonyl group, and d is an integer between 0 and 18, preferentially between 0 and 12 and in particular between 0 and 6.

In particularly preferred embodiments of the invention, $R^1$ represents a C1-C18, preferably C1-C6, linear, branched and/or cyclic alkyl group, optionally interrupted and/or substituted by one or more heteroatoms and/or more groups including at least one heteroatom.

The compound according to the invention may for example comply with the general formula (I'a):

(I'a)

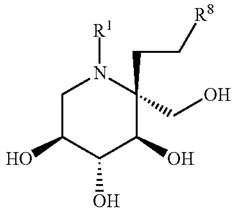

wherein:

$R^1$ represents a hydrogen atom or a C1-C18, preferably C1-C12, in particular

C1-C6, for example C1-C3 and more particularly C1-C2, linear, branched and/or cyclic alkyl group, said alkyl group optionally being interrupted and/or substituted by one or more heteroatoms and/or one or more groups including at least one heteroatom, $R^8$ represents:

a hydrogen atom;

a hydroxyl group;

a methyl, ethyl, propyl, butyl, pentyl, hexyl, cycloalkyl, adamantyl, alkylcycloalkyl, alkylaryl or aryl radical, said radical optionally being interrupted and/or substituted by one or more heteroatoms and/or one or more groups including at least one heteroatom;

a $-Si(R^{12})_3$ group wherein $R^{12}$ represents a hydroxyl radical, a C1-C4 alkyl radical, a C1-C4 alkoxyl radical or a phenyl radical;

a $-(CH_2)_f-Y-R^{13}$ group wherein f is an integer between 0 and 6, Y is a heteroatom selected from oxygen, nitrogen and sulfur and $R^{13}$ represents a C1-C18, preferably C1-C12 and in particular C1-C6, alkyl radical, or an aryl or heteroaryl radical, preferably C1-C18, preferably C1-C12 and in particular C1-C6;

a $-(CH_2)_g-CO-R^{13}$ group wherein g is an integer between 0 and 6 and $R^{13}$ is as defined above;

or a $-(CH_2)_h-SO_e-R^{13}$ group wherein h is an integer between 0 and 6 and e is equal to 1 or 2, and $R^{13}$ is as defined above;

$R^8$ not representing a hydrogen atom when $R^1$ represents a propyl radical.

The compound according to the invention may comply with the general formula (I"a):

(I"a)

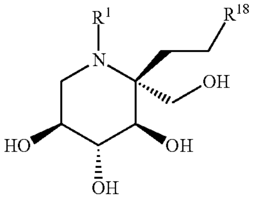

wherein $R^1$ represents a hydrogen atom or a C1-C18 linear, branched and/or cyclic alkyl group, optionally interrupted and/or substituted by one or more heteroatoms and/or one or more groups including at least one heteroatom, $R^{18}$ represents a linear, branched and/or cyclic hydrocarbon radical, saturated or unsaturated, aromatic or not, optionally substituted, comprising from 4 to 18 carbon atoms, preferably from 4 to 12 carbon atoms, and preferentially from 5 to 12 carbon atoms, optionally comprising one or more heteroatoms and/or one or more groups including at least one heteroatom and optionally comprising a single ring or a plurality of rings optionally fused.

$R^{18}$ may in particular represent a butyl, pentyl, hexyl, cyclohexyl, phenyl, benzyl or adamantyl group.

Particular compounds according to the invention are the compounds of formulae (IIa), (IIb), (IIb1), (IIb2), (IIb3), (IIb4), (IIb5), (IIb6), (IIb7), (IIc), (IIc1), (IId), (IIo), (IIp), (IIp1), (IIq), (IIr), (IIs), (IIt), (IIu), (IIv), (IIw), (IIw1), (IIx), (IIx1), and (IIy) described above.

In alternative embodiments of the invention, the compound complies with the general formula (I'b):

(I'b)

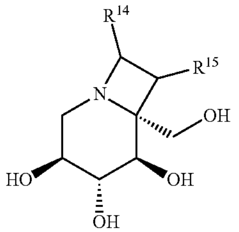

wherein $R^{14}$ represents a hydrogen atom, a carbonyl radical or an alkyl, alkenyl, alkynyl, or alkylaryl radical, such as a benzyl or a C1-C18, preferably C1-C12 and in particular C1-C6, aryl radical, said radical optionally being interrupted and/or substituted by one or more heteroatoms and/or one or more groups including at least one heteroatom; an example of such a radical complies with the formula —$CH_2$-TMS, where TMS represents a trimethylsilyl residue;

and $R^{15}$ represents a hydrogen atom, a hydroxyl radical, an amino radical or a C1-C18, preferably C1-C12 and in particular C1-C6, alkyl, alkenyl or aryl radical, said radical optionally being interrupted and/or substituted by one or more heteroatoms and/or one or more groups including at least one heteroatom.

Particular compounds complying with this definition are the compounds of formulae (IIh), (IIz1), (IIz2), (IIz3), (IIz4) and (IIz5) described above.

In other variants of the invention, the compound complies with the general formula (I'c):

(I'c)

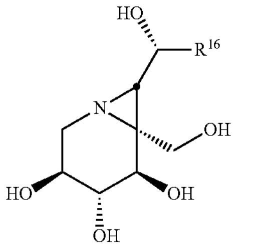

wherein $R^{16}$ represents a hydrogen atom or a C1-C18, preferably C1-C12 and preferentially C1-C6, alkyl radical, said radical optionally being interrupted and/or substituted by one or more heteroatoms and/or one or more groups including at least one heteroatom.

In particular, $R^{16}$ may represent a —$CH_2$—OH group, a methyl radical or an ethyl radical.

Particular compounds complying with this definition are the compounds of formulae (IIj) and (IIk) described above.

All the compounds according to the invention, complying with the general formula (I'), can advantageously be used as drugs in accordance with the present invention, in particular for treating Pompe disease.

The compounds of general formula (I) used according to the invention, in particular the compounds complying with the general formula (I') as defined above, can be synthesized by any method conventional per se for a person skilled in the art. It falls in particular within the competence of a person skilled in the art to determine, for each particular compound, which starting products to use and which synthesis method to apply.

The present invention furthermore relates to novel synthesis methods, which have been developed by the inventors for preparing compounds of general formula (I), and in particular of general formula (I').

Some of the preparation methods according to the invention make it possible to obtain compounds of general formula (I') wherein $R^1$ and $R^2$ are independent from one another, in particular complying with the general formula (I'a) or with the general formula (I"a) as above.

One example of such a particular preparation method according to the invention comprises successive steps of:

a/ reacting a compound of general formula (III) or (IV):

(III)

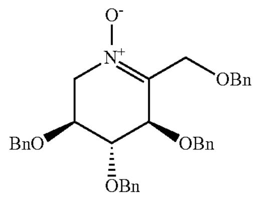

(IV)

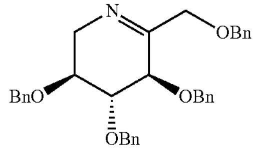

wherein Bn represents a benzyl radical, with a compound of general formula (V):

(V)

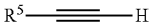

wherein $R^8$ is as defined above with reference to the compound of general formula (I') according to the invention, $R^8$ however representing neither a hydrogen atom nor a hydroxyl group —OH, nor an amino group —$NH_2$, in the presence of an organometallic compound, b/ optionally, reducing the hydroxylamine function into amine, c/ optionally, alkylation of the nitrogen atom of the piperidine ring, d/ and hydrogenolysis of the product obtained at the end of step where applicable step b/ or step c/, in particular for achieving the cleavage of the benzyl radicals to form hydroxyl groups, and where applicable the transformation of the hydroxylamine function into amine and the hydrogenation of the triple bond.

The organometallic compound used for the step a/ may be an organozinc, organolithium, organomagnesium, organoalane, organocopper, etc. compound, or any one of the mixtures thereof. Preferentially, in step a/, the reaction is implemented in the presence of dialkylzinc, in particular diethylzinc $Et_2Zn$, or butyllithium.

More generally, the organometallic compound may comply with the general formula (VII):

$$R^{17}—M \qquad (VII)$$

wherein $R^{17}$ represents a C1-C18 alkyl, alkenyl, alkynyl, alkylaryl or aryl radical, said radical optionally being interrupted and/or substituted by one or more heteroatoms and/or one or more groups including at least one heteroatom, and M represents a metal element such as lithium, zinc, copper, aluminum or magnesium, or M represents Mg—$X^2$, where $X^2$ represents a halogen atom.

The step b/ of reducing the hydroxylamine function into amine and the step c/ of N-alkylation can be implemented according to any method conventional per se for a person skilled in the art.

The step d/ of hydrogenolysis may also be performed by any method conventional per se for a person skilled in the art, in particular by catalytic hydrogenation.

Entirely surprisingly and advantageously, such a method makes it possible to prepare compounds of general formula (I'), in particular of general formula (I'a) or of general formula (I"a), completely stereoselectively.

Examples of such methods can be represented by the synthesis schemes 1 shown on FIG. 1, for the particular example of a compound complying with the general formula (I'a).

Compounds of general formula (I'a) or (I"a) may otherwise, for example, be prepared by a method comprising successive steps of:

a/ cycloaddition reaction of a compound of general formula (III) with trimethylsilylacetylene, b/ reaction of the cycloadduct obtained with a fluoride such as tetrabutylammonium fluoride, for example by a protocol similar to the one described in the publication of Ahn, et al., 1994, J. Org. Chem. 59: 6282-6286, c/ reduction by a metal hydride such as boron and sodium hydride ($NaBH_4$), lithium and aluminum hydride ($LiAlH_4$) or diisobutylaluminum hydride (DIBAL-H), or by a borane such as a dimethylsulfide-borane complex ($BH_3Me_2S$), a borane-tetrahydrofuran complex ($BH_3THF$), a borane-pyridine complex ($BH_3$pyridine), diborane $B_2H_6$, lithium and aluminum hydride ($LiAlH_4$) being particularly preferred, d/ optionally, a step of O-alkylation, O-acylation or O-sulfonylation, which can be implemented according to any method conventional per se for a person skilled in the art, e/ optionally, a step of N-alkylation, which can be implemented according to any method conventional per se for a person skilled in the art, f/ and hydrogenolysis of the product obtained at the end of step c/, where applicable step d/ or step e/, in particular for implementing the cleavage of the benzyl radicals to form hydroxyl groups.

This synthesis method is particularly advantageous in that:

the step a/ is simple to implement and completely regio- and diastereoselective in favor of a product of D-gluco configuration;

the cycloadduct formed in step a/ is easily and effectively transformed into β-lactam, itself easily and effectively reduced into piperidine-alcohol (the β-lactam obtained may otherwise be transformed into a saturated 4-membered ring, by reduction by a silane or by reducing alkylation in the presence of metal catalysts).

One example of such a method can be represented by the synthesis scheme 2 shown on FIG. 2 for the particular example of a compound complying with the general formula II'a).

Compounds of formula (I'd) above can be prepared by a method comprising the reaction of a compound of formula (III) or (IV) as above with a compound of general formula (VI):

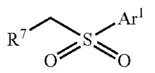

(VI)

in the presence of a lithiated base such as lithium diisopropylamide (LDA) or lithium bis(trimethylsilyl)amide (LiHMDS), preferably in the presence of LiHMDS at low temperature, preferably −78° C.; then, after optionally a step of reducing the hydroxylamine function into amine, and optionally a step of alkylation of the nitrogen atom of the piperidine ring, hydrogenolysis of the product obtained.

An example of such a method can be represented by the synthesis scheme 3 shown in FIG. 3, for the particular example of a compound complying with the general formula (I'd).

Compounds of general formula (I) and in particular of general formula (I') can otherwise, for example, be prepared, from compounds of formula (III) or (IV), by a method comprising the successive steps of:

a/ reaction with a compound of general formula (VII), in particular in the presence of a Lewis acid:

$$R^{17}—M \qquad (VII)$$

wherein $R^{17}$ represents a C1-C18 alkyl, alkenyl, alkynyl, alkylaryl or aryl radical, said radical optionally being interrupted and/or substituted by one or more heteroatoms and/or one or more groups including at least one heteroatom, and M represents a metal element such as lithium, zinc, copper, aluminum or magnesium, or M represents Mg—$X^2$, where $X^2$ represents a halogen atom.

b/ then, optionally, reduction of the hydroxylamine function into amine, in accordance with any method conventional per se for a person skilled in the art, in particular by treatment with zinc powder in an acid medium, c/ then, optionally, alkylation of the nitrogen atom of the piperidine ring, by any method conventional per se for a person skilled in the art, d/ then, optionally, a step of cyclizing metathesis of olefins catalyzed by a complex based on ruthenium, preferentially the 2nd generation Grubbs catalyst, e/ and finally, hydrogenolysis of the product obtained at the end of step a/, where applicable at the end of step b/, of step c/, or of step d/, according to any method conventional per se for a person skilled in the art, in particular in the presence of hydrogen and of a catalytic quantity of palladium on carbon, in an acid medium.

The synthesis route used for obtaining compounds complying with the general formula (I) falls under the general synthesis scheme 4 shown on FIG. 4.

Other preparation methods according to the invention make it possible to obtain compounds of general formula (I') wherein $R^1$ and $R^2$ form together, with the atoms of the piperidine ring to which each is attached, a 4-membered heterocycle fused with the piperidine ring.

Examples of such methods comprise successive steps of:

a/ cycloaddition reaction of a compound of general formula (III) with trimethylsilylacetylene, followed by a reaction with a fluoride such as tetrabutylammonium fluoride, for example according to a protocol similar to the one previously described in the publication by Ahn, et al., 1994, J. Org. Chem. 59: 6282-6286; then either b/ reduction of β-lactam carbonyl by a silane such as phenylsilane $PhSiH_3$, in the presence of a catalyst based on rhodium such as $[Rh(COD)_2]BF_4$ and of 1,3-bis(diphenylphosphino)propane, according to a protocol similar to the one previously described in the publication by Bornschein et al., 2015, Eur. J. Org. Chem, 1915-1919;

or b'/ reducing alkylation of β-lactam carbonyl by reaction with tetramethyldisiloxane in the presence of Vaska's catalyst at ambient temperature, and then addition of a compound of formula (VII) as defined above, at −78° C., according to a protocol similar to the one described in the publication by Xie and Dixon, 2017, Chem. Sci. 8: 7492-7497;

and finally c/ hydrogenolysis of the product obtained at the end of step b/ or b'/, in particular for cleavage of the benzyl radicals to form hydroxyl groups.

The step c/ of hydrogenolysis can be implemented according to any method conventional per se for a person skilled in the art, in particular by catalytic hydrogenation.

The steps b/ and b'/ are particularly advantageous, and novel, in that they make it possible to implement the reduction or the reducing alkylation of a β-lactam the nitrogen atom of which is included in a piperidine ring, to form a heterocycle of the conidine type.

Examples of such methods can be represented by the synthesis scheme 5 shown on FIG. 5, for the particular example of a compound complying with the general formula (I'b).

Another example of such a method comprises successive steps of:

a/ Kinugasa reaction, as described in the reviews by Stecko et al., 2014, Tetrahedron 70: 7817-7844 or by Khangarot & Kaliappan, 2013, Eur. J. Org. Chem. 7664-7677, of a compound of general formula (III) with a compound of general formula (VIII):

(VIII)

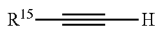

wherein $R^{15}$ represents a C1-C18 alkyl, alkenyl or aryl radical, optionally interrupted and/or substituted by one or more heteroatoms and/or one or more groups including at least one heteroatom, in the presence of a Cu(I) salt and an amine; then b/ reducing alkylation of β-lactam carbonyl by reaction with tetramethyldisiloxane in the presence of Vaska's catalyst at ambient temperature, then addition of a compound of formula (VII) as defined above, at −78° C., according to a protocol similar to the one described in the publication by Xie and Dixon, 2017, Chem. Sci. 8: 7492-7497; and finally c/ hydrogenolysis of the product obtained at the end of the step b/, in particular for implementing the cleavage of the benzyl radicals to form hydroxyl groups. The step c/ of hydrogenolysis can be implemented according to any method conventional per se for a person skilled in the art, in particular by catalytic hydrogenation.

Step b/ is particularly advantageous, and novel, in that it makes it possible to implement the reducing alkylation of a β-lactam the nitrogen atom of which is included in a piperidine ring, to form a heterocycle of the conidine type.

An example of such a method can be represented by the synthesis scheme 6 shown on FIG. 6, for the particular example of a compound complying with the general formula (I'b).

Other preparation methods according to the invention make it possible to obtain compounds of general formula (I') wherein $R^1$ and $R^2$ form together, with the atoms of the piperidine ring to which each is attached, a 3-membered heterocycle fused with the piperidine ring.

An example of such a method comprises successive steps of:

a/ cycloaddition reaction of a compound of general formula (111) or of a compound of general formula (III'):

(III')

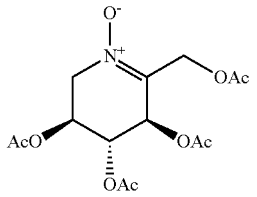

wherein Ac represents an acetyl radical, with a compound of general formula (V) as described above, wherein $R^8$ is as defined above with reference to the compound of general formula (I') according to the invention, $R^8$ however representing neither a hydrogen atom nor a hydroxyl group —OH, nor an amino radical $—NH_2$, b/ thermal Baldwin rearrangement, according to a protocol similar to the one described in the publication by Tangara et al., 2017, Org. Lett. 19: 4842-4845, making it possible to form an acylaziridine, this step preferentially being implemented at 110° C. under irradiation by microwave radiation, c/ reduction of the acylaziridine carbonyl thus obtained by reaction with a metal hydride, preferentially $LiAlH_4$ or $NaBH_4$, d/ and debenzylation, according to any method conventional per se for a person skilled in the art, in particular by Birch reduction in the presence of metals dissolved in liquid ammonia at low temperature, preferably at −78° C., the metal used preferably being lithium.

An example of such a method can be represented by the synthesis scheme 7 shown in FIG. 7, for the particular example of compounds complying with the general formula (I'c).

An example of a method for preparing compounds of general formula (I'e) as above can be represented by the synthesis scheme 8 shown on FIG. 8, with $R^{20}$ being identical to $R^{19}$, $R^{20}$ however not representing a hydrogen atom.

BRIEF DESCRIPTION OF THE DRAWINGS

The features and advantages of the invention will emerge more clearly in the light of the following example embodiments, provided by simple way of illustration and in no way limitative of the invention, with the support of FIGS. 1 to 8, wherein.

DESCRIPTION OF THE PREFERRED EMBODIMENTS

A/ Synthesis and Characterization of Compounds Used in Accordance With the Invention All the reactions were conducted under inert atmosphere in previously dried glassware, under stirring by a magnetic bar, the assembly being placed above a magnetic stirrer, except in the case of reactions under irradiation by microwave. The latter were implemented in sealed tubes equipped with a magnetic bar placed in a microwave reactor, at a temperature regulated by an internal infrared probe. The toluene, the ether and the dichloromethane used as reaction solvents were previously filtered on an Inert PureSolv® purification system. The acetonitrile and dichloroethane were distilled on $CaH_2$. The THF was distilled on sodium in the presence of benzophenone. The commercial reagents, the methanol and the ethanol were used without purification. The reactions were followed by thin-layer chromatography (TLC) by means of silica on aluminum plates (Merck, Kieselgel 60 F254), with revelation under ultraviolet radiation and then by a 3% solution of potassium permanganate in a 10% solution of potassium hydroxide (w/v). The purifications by column chromatography were implemented by means of Macherey-Nagel® Silica Gel 60 (70-230 mesh). The rotatory powers were measured on a PerkinElmer 341 polarimeter. The infrared spectra were obtained on a Nicolet "Magna 550" spectrometer including an ATR (attenuated total reflexion) module on which the products were deposited pure, in the solid or liquid state. The data are expressed in $cm^{-1}$. The $^1H$ NMR and $^{13}C$ NMR {DEPT-Q} were obtained with Avance 500 ($^1H$: 500 MHz, $^{13}C$: 125 MHz) or Avance 400 (1H: 400 MHz, $^{13}C$: 100 MHz) spectrometers. The chemical shifts for the $^1H$ spectra are expressed with respect to those of the residual solvents contained in $CDCl_3$ (δ7.26 ppm) or $CD_3OD$ (δ 3.31 ppm). The chemical shifts for the $^{13}C$ spectra are expressed with respect to those of the solvents $CDCl_3$ (δ 77.16 ppm) or $CD_3OD$ (δ 49.00 ppm). The $^1H$ NMR spectra are reported as follows: chemical shift (ppm), multiplicity (br: broad; s: singulet; d: doublet; dd: doublet of doublets; t: triplet; pst: pseudo triplet; m: multiplet), coupling constants (Hz) and integration. The high-resolution mass spectra (HRMS) were recorded on a Thermo Scientific ESI/LTQ Orbitrap XL® or Waters G2-S Q-TOF mass spectrometer.

A.1/Synthesis Methods 1

Figure 1:
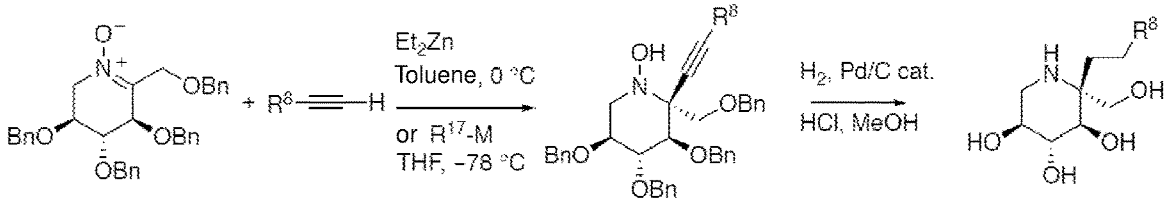
FIG. 1 shows a first example of general synthesis schemes (synthesis scheme 1) for preparing compounds of formula (I'a) according to the invention.

The synthesis methods used for obtaining compounds complying with the above general formula (I'a) falls under the general synthesis schemes shown on FIG. 1.

1) General Protocol A—Alkynylation of the Nitrone of Formula (III) Leading to the Propargylic Hydroxylamines of Formula A-1

A 1M solution of diethyl zinc in hexane (1.5 equiv.) is added dropwise to an alkyne solution of formula (V) (4 equiv.) in anhydrous toluene at 0° C. under argon atmosphere. The resulting mixture is stirred for 30 minutes at 0° C. A solution of ketonitrone of formula (III) (1 equiv.) in anhydrous toluene is then added dropwise at 0° C., and then the reaction mixture is stirred until the reaction is complete (followed by TLC). A saturated aqueous solution of $NaHCO_3$ is added and then the resulting mixture is diluted with diethylether. The organic phase is separated and the aqueous phase is extracted twice with diethylether. The organic phases are washed with brine, dried on $MgSO_4$ and evaporated under reduced pressure. The hydroxylamines of formula A-1 thus formed are purified by silica gel chromatography, before being reduced and debenzylated in accordance with the following general protocol B.

2) General Protocol A'—Alkynylation of the Nitrone of Formula (III) Leading to the Propargylic Hydroxylamines of Formula A-1.

A 1.4 M solution of n-butyllithium in hexane (2.5 equiv.) is added dropwise to a solution of alkyne of formula (V) (2.5 equiv.) in anhydrous THF at −10° C. under argon atmosphere. The resulting solution is stirred for 15 minutes at −10° C. and is then cooled to −78° C. A solution of ketonitrone of formula (III) (1 equiv.) in anhydrous THF is then added dropwise at −78° C., and then the reaction mixture is stirred until the reaction is complete (followed by TLC). A saturated aqueous solution of $NH_4Cl$ is added and the mixture is allowed to rise to ambient temperature, and then extracted three times by ethyl acetate. The organic phases are collected and washed with brine, dried on $MgSO_4$ and concentrated under reduced pressure. The hydroxylamines of formula A-1 thus isolated are purified by silica gel chromatography, before being reduced and debenzylated in accordance with the following general protocol B.

3) General Protocol B 1.5 equiv. of hydrochloric acid HCl (2M solution in anhydrous ether) and 0.2 equiv. of Pd/C 10% are added to a solution of O-benzylated iminosugar (1 equiv.) in absolute ethanol. The suspension obtained is stirred at room temperature for 17 hours under pressure of hydrogen (5 bar) and then filtered on Celite®. The Celite® is rinsed with methanol and the filtrate is concentrated at reduced pressure to give an iminosugar hydrochlorate. This salt is purified on Dowex® 50W-X2 ion exchange resin previously activated by HCl, and eluted with aqueous $NH_4OH$, to obtain after evaporation of the solvents the corresponding neutral compound of formula (I'a).

Compound of Formula (IIc)

The compound of above formula (IIc) ((2R,3R,4R,5S)-2-(hydroxymethyl)-2-phenethylpiperidine-3,4,5-triol: 36.7 mg; 73% for 2 steps) was prepared in accordance with the general procedures A and B, from nitrone of formula (III) (110.0 mg, 0.205 mmol) and phenylacetylene (Va: $R^8$=Ph, 0.034 mL; 0.307 mmol).

A solid yellow is obtained, with the following characteristics:

$[\alpha]^{20}_D$+4.7 (c 0.98, $CH_3OH$);

IR ν 3291, 2918, 2864, 1632, 1494, 1455, 1363, 1270, 1198, 1094, 1076, 1040, 1004 $cm^{-1}$;

$^1H$ NMR (500 MHz, $CD_3OD$) δ 7.31-7.08 (m, 5H), 3.73 (d, J=10.4 Hz, 1H), 3.55 (d, J=10.5 Hz, 1H), 3.55-3.43 (m, 2H), 3.45-3.34 (m, 1H), 3.00-2.90 (m, 1H), 2.68-2.51 (m, 3H), 1.91-1.72 (m, 2H) ppm;

$^{13}C$ NMR (125 MHz, $CD_3OD$) δ 144.4 ($^{Ar}$Cq), 129.4 ($^{Ar}$CH), 129.3 ($^{Ar}$CH), 126.7($^{Ar}$CH), 76.5 (CH), 75.2 (CH), 73.8 (CH), 65.6 ($CH_2$), 60.5 (Cq), 45.9 ($CH_2$), 30.7 ($CH_2$), 29.9 ($CH_2$) ppm;

HRMS ($ESI^+$) Calc. $C_{14}H_{22}NO_4$ $[M+H]^+$: m/z=268.15433; Found m/z=268.15372.

Compound (IIx1)

The compound of above formula (IIx1) ((2R,3R,4R,5S)-2-(hydroxymethyl)-2-(2-(trimethylsilyl)ethyl)piperidine-3,4,5-triol: 7.1 mg; 29% for 2 steps) was prepared in accordance with the general procedures A and B, from nitrone of formula (III) (102.1 mg, 0.189 mmol) and trimethylsilylacetylene (Vb: $R^8$=TMS, 0.105 mL; 0.759 mmol).

A white foam is obtained, with the following characteristics:

$[\alpha]^{20}$D+4.51 (c 0.71, MeOH);

$^1H$ NMR (400 MHz, $CD_3OD$) δ 3.57 (d, J=10.9 Hz, 1H), 3.52 (d, J=9.3 Hz, 1H), 3.44 (t, J=4.0 Hz, 1H), 3.39 (d, J=10.0 Hz, 1H), 3.39-3.33 (m, 1H), 2.85 (dd, J=12.8, 5.5 Hz, 1H), 2.42 (dd, J=12.8, 10.8 Hz, 1H), 1.62-1.51 (m, 2H), 0.56-0.44 (m, 1H), 0.39-0.29 (m, 1H), 0.02 (s, 9H) ppm;

$^{13}C$ NMR (100 MHz, $CD_3OD$) δ 76.6 (CH), 75.5 (CH), 73.8 (CH), 65.6 ($CH_2$), 60.5 (Cq), 45.8 ($CH_2$), 21.0 ($CH_2$), 8.60 ($CH_2$), −1.86 ($CH_3$) ppm;

HRMS ($ESI^+$) Calc. $C_{11}H_{26}NO_4Si$ $[M+H]^+$: m/z=264.16256; Found m/z=264.16282.

Compound (IIr)

The compound of above formula (IIr) ((2R,3R,4R,5S)-2-(2-((3R,5R,7R)-adamantan-1-ypethyl)-2-(hydroxymethyl) piperidine-3,4,5-triol: 15.0 mg; 27% for 2 steps) was prepared in accordance with the general procedures A' and B, from nitrone of formula (III) (100 mg, 0.185 mmol) and adamantylacetylene (Vh: $R^8$=adamantyl, 74.5 mg, 0.465 mmol).

A yellowish lacquer is obtained, with the following characteristics:

$[\alpha]^{20}_D$+7.46 (c 0.63, MeOH);

$^1H$ NMR (500 MHz, $CD_3OD$) δ 3.79 (d, J=10.9 Hz, 1H), 3.64-3.48 (m, 4H), 3.11 (br d, J=11.3 Hz, 1H), 2.78-2.66 (m, 1H), 2.00-1.91 (m, 3H), 1.82-1.63 (m, 8H), 1.58-1.49 (m, 6H), 1.19-1.03 (m, 2H) ppm;

$^{13}C$ NMR (100 MHz, $CD_3OD$) δ 74.9 (CH), 72.5 (CH), 70.8 (CH), 63.7 (Cq), 62.5 ($CH_2$), 44.2 ($CH_2$), 43.3 ($CH_2$), 38.2 ($CH_2$), 37.0 ($CH_2$), 30.1 (CH), 20.7 ($CH_2$) ppm;

HRMS ($ESI^+$) Calc. $C_{18}H_{31}NO_4$ $[M+H]^+$: m/z=326.23258; Found m/z=326.23225.

Compound (IIb7)

The compound of above formula (IIb7) ((2R,3R,4R,5S)-2-(2-cyclohexylethyl)-2-(hydroxymethyl)piperidine-3,4,5-triol: 57.3 mg; 59% for 2 steps) was prepared in accordance with the general procedures A and B, from nitrone of formula (III) (99.8 mg; 0.185 mmol) and 1-ethynylcyclohexene (Vd: $R^8$=cyclohexene; 87 μL; 0.742 mmol).

A white solid is obtained, with the following characteristics:

$[\alpha]^{20}_D$+3.63 (c 1.43, MeOH);

$^1H$ NMR (400 MHz, $CD_3OD$) δ 3.60 (d, J=10.6 Hz, 1H, $^7CH_2$), 3.52-3.43 (m, 2H, $^3$CH, $^4$CH), 3.43-3.33 (m, 2H), 2.87 (dd, J=12.8, 5.0 Hz), 2.49 (ps t, J=11.7 Hz, 1H), 1.83-1.62 (m, 5H), 1.60-1.47 (m, 2H), 1.34-1.06 (m, 6H), 1.01-0.86 (m, 2H) ppm;

$^{13}C$ NMR (100 MHz, $CD_3OD$) δ 76.5 (CH), 75.1 (CH), 73.8 (CH), 65.5 ($CH_2$), 60.3 (Cq), 45.8 ($CH_2$), 39.9 (CH), 34.6 ($CH_2$), 34.5 ($CH_2$), 30.6 ($CH_2$), 27.8 ($CH_2$), 27.5 ($CH_2$), 24.8 ($CH_2$) ppm;

HRMS ($ESI^+$) Calc. $C_{14}H_{20}NO_4$ $[M+H]^+$: m/z=274.20128; Found m/z=274.20139.

Compound (IIb1)

The compound of above formula (IIb1) ((2R,3R,4R,5S)-2-(hydroxymethyl)-2-pentylpiperidine-3,4,5-triol: 32.8 mg; 67% for 2 steps) was prepared in accordance with the general procedures A and B, from nitrone of formula (III) 96.8 mg; 0.180 mmol) and 1-pentyne (Ve: $R^8$=$C_3H_7$; 71 μL; 0.720 mmol).

A yellow solid is obtained, with the following characteristics:

$[\alpha]^{20}_D$−1.29 (c 1.01, MeOH);

$^1H$ NMR (400 MHz, $CD_3OD$) δ 3.61 (d, J=10.6 Hz, 1H), 3.52-3.33 (m, 4H), 2.87 (dd, J=12.8, 5.3 Hz, 1H), 2.49 (ps t, J=11.8 Hz, 1H), 1.62-1.43 (m, 2H), 1.43-1.17 (m, 6H), 0.92 (t, J=6.7 Hz, 3H) ppm;

$^{13}C$ NMR (100 MHz, $CD_3OD$) δ 76.5 (CH), 75.2 (CH), 73.9 (CH), 65.7 ($CH_2$), 60.2 (Cq), 45.9 ($CH_2$), 33.9 ($CH_2$), 27.7 ($CH_2$), 23.6 ($CH_2$), 22.9 ($CH_2$), 14.4 ($CH_3$) ppm; HRMS ($ESI^+$) Calc. $C_{11}H_{24}NO_4$ [M+H]+: m/z=234.16998; Found m/z=234.17004.

Compound (IIb3)

The compound of above formula (IIb3) ((2R,3R,4R,5S)-2-heptyl-2-(hydroxymethyl)piperidine-3,4,5-triol: 33.2 mg; 69% for 2 steps) was prepared in accordance with the general procedures A and B, from nitrone of formula (III) (100.7 mg; 0.187 mmol) and 1-heptyne (Vf: $R^8$=$C_5H_{11}$; 98 μL; 0.749 mmol).

A yellow solid is obtained, with the following characteristics:

$[\alpha]^{20}_D$+1.04 (c 0.96, MeOH);

1H NMR (400 MHz, $CD_3OD$) δ 3.61 (d, J=10.6 Hz, 1H), 3.51-3.44 (m, 2H), 3.41 (d, J=10.8 Hz), 3.39-3.33 (m, 1H), 2.87 (dd, J=13.0, 5.4 Hz, 1H), 2.49 (ps t, J=11.4 Hz, 1H), 1.58-1.47 (m, 2H), 1.43-1.18 (m, 10H), 0.90 (t, J=6.2 Hz, 3H) ppm;

$^{13}C$ NMR (100 MHz, $CD_3OD$) δ 76.5 (CH), 75.1 (CH), 73.8 (CH), 65.6 ($CH_2$), 60.3 (Cq), 45.9 ($CH_2$), 33.0 ($CH_2$), 31.7 ($CH_2$), 30.4 ($CH_2$), 23.7 ($CH_2$), 23.2 ($CH_2$), 27.8 ($CH_2$), 14.4 ($CH_3$) ppm;

HRMS ($ESI^+$) Calc. $C_{13}H_{28}NO_4$ $[M+H]^+$: m/z=261.20128; Found m/z=261.20131.

Compound (IIc1)

The compound of above formula (IIc1) ((2R,3R,4R,5S)-2-(hydroxymethyl)-2-(3-phenylpropyl)piperidine-3,4,5-triol: 20.2 mg; 45% for 2 steps) was prepared according to the general procedures A and B, from nitrone of formula (III) (96.7 mg; 0.179 mmol) and 3-phenyl-1-propyne (Vg: $R^8$=$CH_2$Ph; 89 μL; 0.719 mmol). A yellow lacquer is obtained, with the following characteristics:

$[\alpha]^{20}_D$+1.68 (c 1.37, MeOH);

$^1$H NMR (400 MHz, $CD_3OD$) δ 7.10-7.10 (m, 5H), 3.60 (d, J=10.6 Hz, 1H), 3.49-3.37 (m, 3H), 3.37-3.32 (m, 1H), 2.84 (dd, J=13.1, 5.4 Hz, 1H), 2.69-2.53 (m, 2H), 2.42 (dd, J=13.0, 10.8 Hz, 1H), 1.75-1.49 (m, 4H) ppm;

$^{13}$C NMR (100 MHz, $CD_3OD$) δ 143.6 ($^{Ar}$Cq), 129.4 ($^{Ar}$CH), 129.3 ($^{Ar}$CH), 126.7 ($^{Ar}$CH), 76.5 (CH), 75.1 (CH), 73.8 (CH), 65.6 ($CH_2$), 60.3 (Cq), 45.8 ($CH_2$), 37.6 ($CH_2$), 27.5 ($CH_2$), 25.3 ($CH_2$) ppm;

HRMS (ESI$^+$) Calc. $C_{15}H_{24}NO_4$ [M+H]+: m/z=282.16998; Found m/z=282.16968.

A.2/ Synthesis Method 2

Figure 2:
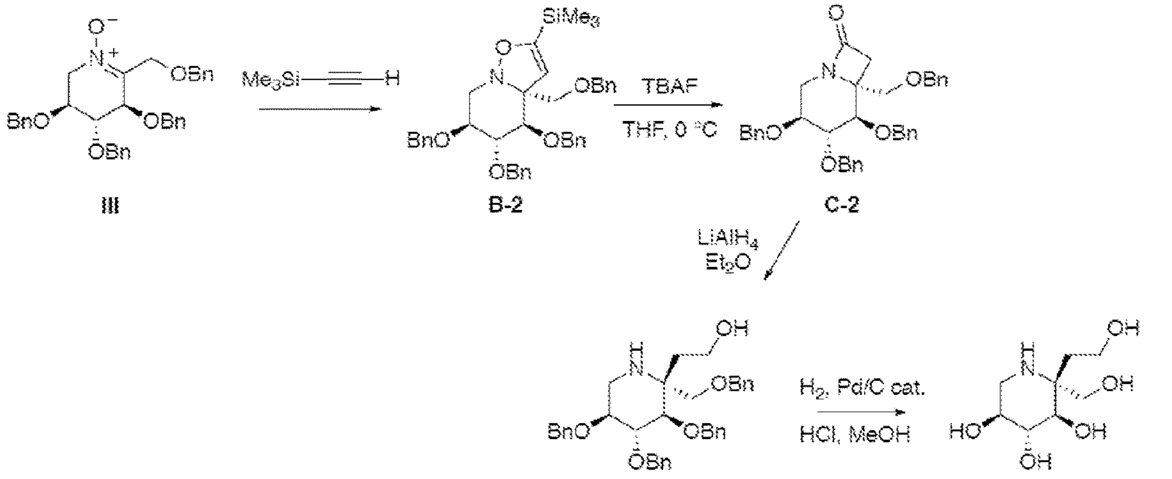
FIG. 2 shows a second example of a general synthesis scheme (synthesis scheme 2) for preparing compounds of formula (I'a) according to the invention.

The synthesis method used for obtaining compounds complying with the general formula (I'a) below falls under the general synthesis scheme 2 shown on FIG. 2.

Compound of Formula (IId)

The compound of above formula (IId) (2R,3R,4R,5S)-2-(2-hydroxyethyl)-2-(hydroxymethyl)piperidine-3,4,5-triol is prepared in the following manner.

A mixture of nitrone (III) (566 mg, 1.05 mmol) and of trimethylsilylacetylene alkyne (Vb: $R^8$=$SiMe_3$, 2.2 mL, 15.75 mmol) was stirred at ambient temperature for 21 hours, and then the excess alkyne was evaporated under reduced pressure. The raw isoxazoline B-2 thus obtained (667 mg, 1.05 mmol) was dissolved in anhydrous THF (20 mL) and a solution of TBAF (1M in THF, 1.05 mL, 1.05 mmol) was added at 0° C. The solution was stirred at 0° C. for 45 minutes, and then $CH_2Cl_2$ and water were added. The aqueous phase was extracted three times with $CH_2Cl_2$. The organic phases were washed with brine, dried on $MgSO_4$, and then the solvents were evaporated under reduced pressure. Purification of the residue obtained by chromatography supplied bicyclic β-lactic C-2 (440.6 mg, 74% in 2 steps). $LiAlH_4$ (9.6 mg, 0.25 mmol) was added at 0° C. to a solution of this β-lactam C-2 (71.3 mg, 0.13 mmol) in ether (1.5 mL). The mixture was stirred at ambient temperature for 2 hours and then diluted with $CH_2Cl_2$, aqueous $NH_4Cl$ and a few drops of aqueous NaOH up to basic pH. The aqueous phase was extracted (three times) with $CH_2Cl_2$. The organic phases were washed with brine, dried on $MgSO_4$, and the solvents were evaporated under reduced pressure to give piperidine D-2 (translucent oil, 61.1 mg, 85%) after purification by chromatography. This compound (26.3 mg, 0.463 mmol) was debenzylated in accordance with the general procedure B to give piperidine (IId) (9.3 mg, 97%). A pale yellow lacquer was obtained, with the following characteristics:

$[\alpha]^{20}_D$+8.2 (c 0.61, $CH_3OH$);

IR ν 3287, 2920, 1644, 1431, 1081 $cm^{-1}$;

$^1$H NMR (500 MHz, $CD_3OD$) δ 1.86 (t, J=6.5 Hz, 2H), 2.65 (dd, J=11.2, 12.6 Hz, 1H), 2.92 (dd, J=5.4, 13.1 Hz, 1H), 3.33-3.43 (m, 2H), 3.48 (d, J=9.1 Hz, 1H), 3.58 (d, J=10.8 Hz, 1H), 3.64-3.76 (m, 3H) ppm;

$^{13}$C NMR (125 MHz, $CD_3OD$) δ 30.5 ($CH_2$), 45.8 ($CH_2$), 58.8 ($CH_2$), 60.9 ($C_q$), 65.7 ($CH_2$), 73.5 (CH), 74.6 (CH), 76.3 (CH) ppm;

HRMS (ESI$^+$) Calc. $C_8H_{18}NO_5$[M+H]$^+$: m/z=208.1185; Found m/z=208.1184.

A.3/ Synthesis Method 3

Figure 3:
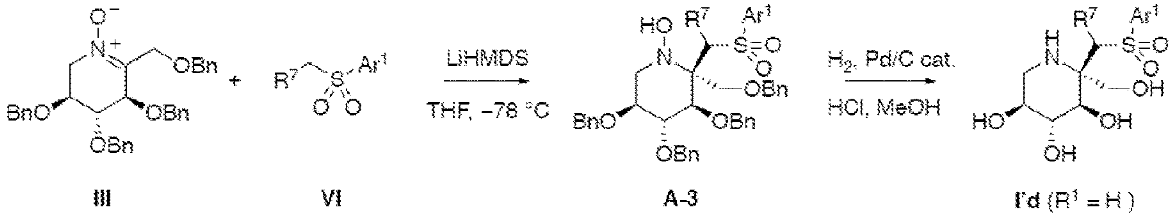
FIG. 3 shows an example of a general synthesis scheme (synthesis scheme 3) for preparing compounds of formula (I'd) according to the invention.

The synthesis method used for obtaining compounds complying with the general formula (I'd) below falls under the general synthesis scheme 3 shown on FIG. 3.

Compound of Formula (IIw)

The compound of above formula (IIw) (2S,3S,4R,5S)-3,4,5-tris(benzyloxy)-2-((benzyloxy)methyl)-2-(pyridin-2-ylsulfonyl)piperidin-1-ol is prepared in the following manner. A solution of nitrone of formula (III) (196 mg; 0.366 mmol) and of 2-pyridyl-methylsulfone (VIa) (74.6 mg; 0.475 mmol) in anhydrous THF (10 mL) under argon atmosphere was cooled to −78° C. 1M LiHMDS in THF (548 μL; 0.548 mmol) was added dropwise and then the reaction mixture was stirred at this same temperature until the reaction was complete. After the addition of water and ethyl acetate, the aqueous phase was extracted (three times) with ethyl acetate. The collected organic phases were washed with brine, dried on $MgSO_4$ and then concentrated at reduced pressure. Purification of the residue obtained by chromatography supplied the compound of formula A-3a ($R^7$=H) 115 mg; 55%). This compound was debenzylated according to a variant of the general procedure B to give piperidine (IIw).

A.4/ Synthesis Methods 4

Figure 4:
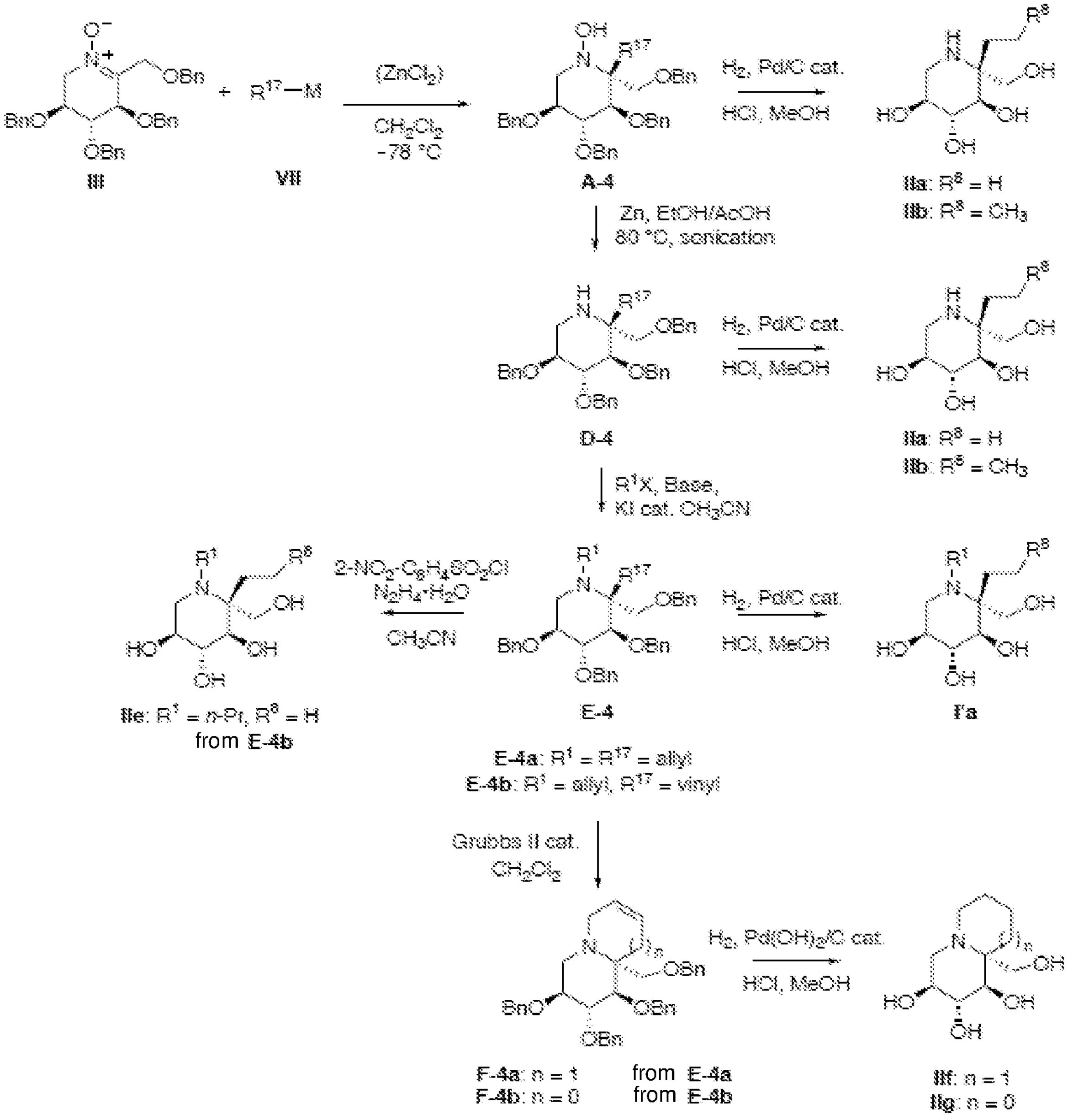
FIG. 4 shows a third example embodiment of general synthesis schemes (synthesis schemes 4) for preparing compounds of formula (I'a) and, more generally, compounds of general formula (I) used according to the invention.

The synthesis methods used for obtaining compounds complying with the general formula (I), in particular compounds complying with the general formula (I'a), below fall under a general synthesis scheme 4 shown on FIG. 4.

Compound of Formula (IIa)

The compound of above formula (IIa) ((2R,3R,4R,5S)-2-ethyl-2-(hydroxymethyl)piperidine-3,4,5-triol) was prepared in accordance with the general protocol B described for the synthesis method 1, from piperidine D-4b ($R^{17}$=vinyl, 74.0 mg, 0.137 mmol), obtained as described in the publication by Boisson et al., 2015, Org. Lett. 17: 3662-3665, and was isolated with a yield of 95% (24.9 mg).

A pale yellow lacquer is obtained, with the following characteristics:

$[\alpha]^{20}_D$+1.6 (c 1.22, $CH_3OH$);

IR ν 3286, 2939, 1643, 1445, 1096 $cm^{-1}$;

$^1$H NMR (500 MHz, $CD_3OD$) δ 0.86 (t, J=7.6 Hz, 3H), 1.55-1.68 (m, 2H), 2.51 (dd, J=10.8, 12.8 Hz, 1H), 2.89 (dd, J=5.4, 13.0 Hz, 1H), 3.34-3.40 (m, 1H), 3.42 (d, J=10.7 Hz, 1H), 3.44-3.51 (m, 2H), 3.62 (d, J=10.7 Hz, 1H) ppm; $^{13}$C NMR (125 MHz, $CD_3OD$) δ 7.0 ($CH_3$), 20.1 ($CH_2$), 45.7 ($CH_2$), 60.5 ($C_q$), 65.0 ($CH_2$), 73.6 (CH), 75.1 (CH), 76.4 (CH) ppm;

HRMS (ESI$^+$) Calc. $C_8H_{17}NO_4$[M+H]$^+$: m/z=192.1236; Found m/z=192.1237.

Compound of Formula (IIb)

The compound of above formula (IIb) ((2R,3R,4R,5S)-2-(hydroxymethyl)-2-propylpiperidine-3,4,5-triol) was prepared in accordance with the general protocol B described for the synthesis method 1, from piperidine D-4a ($R^{17}$=allyl, 39.7 mg, 0.071 mmol), obtained as described in the publication by Vieira Da Cruz et al., 2017, J. Org. Chem. 82: 9866-9872, and was isolated with a yield of 79% (11.4 mg).

A colorless lacquer is obtained, with the following characteristics:

$[\alpha]^{20}_D$+5.4 (c 0.55, $CH_3OH$);

IR ν 3291, 2932, 1625, 1454, 1090 $cm^{-1}$;

$^1$NMR (500 MHz, $CD_3OD$) δ 0.94 (t, J=7.2 Hz, 3H), 1.22-1.42 (m, 2H), 1.49-1.57 (m, 2H), 2.53 (dd, J=10.8, 13.0 Hz, 1H), 2.89 (dd, J=5.5, 13.0 Hz, 1H), 3.34-3.41 (m, 1H), 3.42 (d, J=10.7 Hz, 1H), 3.45-3.51 (m, 2H), 3.64 (d, J=10.7 Hz, 1H) ppm;

$^{13}$C NMR (125 MHz, $CD_3OD$) δ 15.3 ($CH_3$), 16.6 ($CH_2$), 30.4 ($CH_2$), 45.7 ($CH_2$), 60.7 (CO, 65.3 ($CH_2$), 73.5 (CH), 74.9 (CH), 76.3 (CH) ppm;

HRMS (ESI$^+$) Calc. $C_9H_{20}NO_4$ $[M+H]^+$: m/z=206.1392; Found m/z=206.1396

Compound of Formula (IIe)

The compound of above formula (IIe) (2R,3R,4R,5S)-2-ethyl-2-(hydroxymethyl)-1-propylpiperidine-3,4,5-triol is prepared in the following manner.

The piperidine E-4b ($R^1$=allyl, $R^{17}$=vinyl; 62 mg, 0.105 mmol), obtained as described in the publication by Boisson et al., 2015, Org. Lett. 17: 3662-3665, was dissolved in anhydrous acetonitrile (0.5 mL), treated with 2-nitrobenzenesulfonyl chloride (186 mg, 0.84 mmol) at 0° C., and then with hydrazine monohydrate (0.08 mL, 1.68 mmol), added dropwise at 0° C. This reaction mixture was maintained under stirring at ambient temperature for 28 hours, and then water was added and the aqueous phase was extracted (3 times) with dichloromethane. The collected organic phases were washed with brine, dried over $MgSO_4$ and concentrated under reduced pressure. After purification by chromatography, a mixture of the products of hydrogenation solely of the allyl group and of hydrogenation of the allyl and vinyl groups was isolated (58 mg, 94%, 3:7 mixture). This mixture was dissolved in methanol (1.5 mL), and then treated with Pearlman's reagent (20% $Pd(OH)_2/C$, 16.8 mg, 0.119 mmol) and HCl (2 M solution in ether, 0.2 mL, 0.4 mmol) under hydrogen atmosphere (1 atm) and under vigorous stirring for 40 hours. The mixture was filtered over Celite®, the Celite® was rinsed several times with methanol, then the filtrate was concentrated under reduced pressure. The residue was solubilized in water and purified on cation exchange resin (DOWEX 50W-X8, form $H^+$; elution by an aqueous solution of 1M $NH_4OH$) to provide the product (IIe) (11.9 mg, 49%). A beige solid is obtained, with the following characteristics:

$[\alpha]^{20}_D$−40.7 (c 0.60, $CH_3OH$);

IR ν 3363, 2962, 2932, 2874, 2826, 1653, 1464, 1379, 1097, 1048, 1016 $cm^{-1}$ $^1H$ NMR (500 MHz, $CD_3OD$) δ□0.90 (t, J=7.5 Hz, 3H), 0.96 (t, J=7.5 Hz, 3H), 1.39-1.50 (m, 1H), 1.51-1.60 (m, 1H), 1.61-1.75 (m, 2H), 2.26-2.34 (m, 1H), 2.42-2.51 (m, 1H), 2.76-2.85 (m, 1H), 2.93-3.00 (m, 1H), 3.40-3.52 (m, 3H), 3,65 (d, J=11.0 Hz, 1H), 3.79 (d, J=11.0 Hz, 1H) ppm;

$^{13}C$ NMR (125 MHz, $CD_3OD$) δ 9.6 ($CH_3$), 11.9 ($CH_3$), 19.2 ($CH_2$), 23.2 ($CH_2$), 52.0 ($CH_2$), 52.2 ($CH_2$), 62.5 ($CH_2$), 71.5 (CH), 74.9 (CH), 76.4 (CH) ppm;

HRMS (ESI$^+$) Calc. $C_{11}H_{24}NO_4$ $[M+H]^+$: m/z=234.1700; Found m/z=234.1696.

Compound of Formula (IIf)

The compound of formula (IIf) as above (1R,2R,3S,9aR)-9a —(hydroxymethyl)octahydro-1H-quinolizine-1,2,3-triol is prepared in the following manner.

Piperidine E-4a ($R^1$=$R^{17}$=allyl; 35 mg, 0.06 mmol), obtained as described in the publication by Vieira Da Cruz et al., 2017, J. Org. Chem. 82: 9866-9872, was dissolved in anhydrous $CH_2Cl_2$ (3 mL). This solution was carefully degassed, and then the Grubbs II catalyst (1.3 mg, 2.5 mol %) was added. The mixture was maintained under stirring at ambient temperature for 20 hours, and then filtered over silica. The silica was rinsed with ethyl acetate and methanol, and the solvents were evaporated under reduced pressure. After purification of the residue thus obtained by chromatography, the product of cyclization by metathesis of F-4a olefins (32 mg, 95%) was isolated. The latter (34 mg, 0.06 mmol) was dissolved in methanol (1 mL), and then treated with Pearlman's reagent (20% $Pd(OH)_2/C$, 14 mg, 0.10 mmol) and HCl (2M solution in ether, 0.045 mL, 0.09 mmol) under hydrogen atmosphere (5 bar) and under vigorous stirring for 17 hours. The mixture was filtered over Celite®, the Celite® was rinsed several times with methanol, and then the filtrate was concentrated under reduced pressure. The residue was dissolved in water and purified over cation exchange resin (DOWEX® 50W-X8, form $H^+$; elution by an aqueous solution of 1M $NH_4OH$) to provide the product (IIf) (9 mg, 73%).

A colorless oil is obtained, with the following characteristics:

$[\alpha]^{20}_D$+16.6 (c 0,41, $CH_3OH$);

IR ν 3336, 2942, 2869, 1053 $cm^{-1}$;

$^1H$ NMR (500 MHz, $CD_3OD$) δ 1.28 (br d, J=11.6 Hz, 1H), 1.37-1.44 (m, 1H), 1.62-1.76 (m, 3H), 1.81-1.94 (m, 1H), 2.66 (dd, J=3.0, 14.0 Hz, 1H), 2.72 (dd, J=4.9, 11.3 Hz, 1H), 3.12 (t, J=11.0 Hz, 1H), 3.20 (pstd, J=3.0, 14.0 Hz, 1H), 3.38 (pst, J=9.3 Hz, 1H), 3.45-3.52 (m, 2H), 3.68 (d, J=11.1 Hz, 1H), 3.95 (d, J=11.1 Hz, 1H) ppm;

$^{13}C$ NMR (125 MHz, $CD_3OD$) δ 18.7 ($CH_2$), 19.2 ($CH_2$), 20.7 ($CH_2$), 48.5 ($CH_2$), 53.3 ($CH_2$), 60.7 ($CH_2$), 62.0 ($C_q$), 71.4 (CH), 74.1 (CH), 75.9 (CH) ppm; HRMS (ESI$^+$) Calc. $C_{10}H_{20}NO_4$ $[M+H]^+$: m/z=218.1392; Found m/z=218.1396.

Compound of Formula (IIg)

The compound of formula (IIg) as above (6S, 7R, 8R, 8aR)-8a —(hydroxymethyl)-octahydroindolizine-6,7,8-triol is prepared in the following manner.

Piperidine E-4b ($R^1$=allyl, $R^{17}$=vinyl; 74 mg, 0.125 mmol), obtained as described in the publication by Boisson et al., 2015, Org. Lett. 17: 3662-3665, was dissolved in anhydrous $CH_2Cl_2$ (6.3 mL). This solution was carefully degassed, and then the Grubbs II catalyst (5.3 mg, 0.006 mmol) was added and the mixture was heated at 40° C. for 3 hours, under stirring. After cooling to ambient temperature, the reaction mixture was filtered over silica, the silica was rinsed with ether, and the solvents were evaporated under reduced pressure. After purification of the residue thus obtained by chromatography, the product of cyclization by metathesis of olefins F-4b (65 mg, 93%) was isolated. The latter (50 mg, 0.089 mmol) was dissolved in methanol (1.4 mL), then treated with Pearlman's reagent (20% $Pd(OH)_2/C$, 17.9 mg, 0.025 mmol) and HCl (2M solution in ether, 0.066 mL, 0.133 mmol) under hydrogen atmosphere (5 bar) and under vigorous stirring for 17 h. The mixture was filtered over Celite®, the Celite® was rinsed several times with methanol, and then the filtrate was concentrated under reduced pressure. The residue was dissolved in water and purified over cation exchange resin (DOWEX 50W-X8, form $H^+$; elution by an aqueous solution of 1M $NH_4OH$) to provide the product (IIg) (16 mg, 89%).

A beige solid is obtained, with the following characteristics:

$[\alpha]^{20}_D$+27.9 (c 0.41, $CH_3OH$);

IR ν 3330, 2924, 1652, 1031 $cm^{-1}$;

$^1H$ NMR (500 MHz, $CD_3OD$) δ 1.46-1.53 (m, 1H), 1.67-1.76 (m, 1H), 1.88-1.96 (m, 1H), 1.98-2.08 (m, 1H), 2.46 (pst, J=11.0 Hz, 1H), 2.80-2.89 (m, 2H), 3.09-3.18 (m, 1H), 3.33-3.41 (m, 2H), 3.43-3.49 (m, 1H), 3.53 (d, J=11.5 Hz, 1H), 3.76 (d, J=9.5 Hz, 1H) ppm;

$^{13}C$ NMR (125 MHz, $CD_3OD$) δ 21.0 ($CH_2$), 26.1 ($CH_2$), 53.8 ($CH_2$), 55.9 ($CH_2$), 63.6 ($CH_2$), 71.0 (CH), 73.0 (CH), 73.2 (Cq), 76.5 (CH) ppm;

HRMS (ESI$^+$) Calc. $C_9H_{18}NO_4$ $[M+H]^+$: m/z=204.1236; Found m/z=204.1234.

A.5/ Synthesis Methods 5

Figure 5:
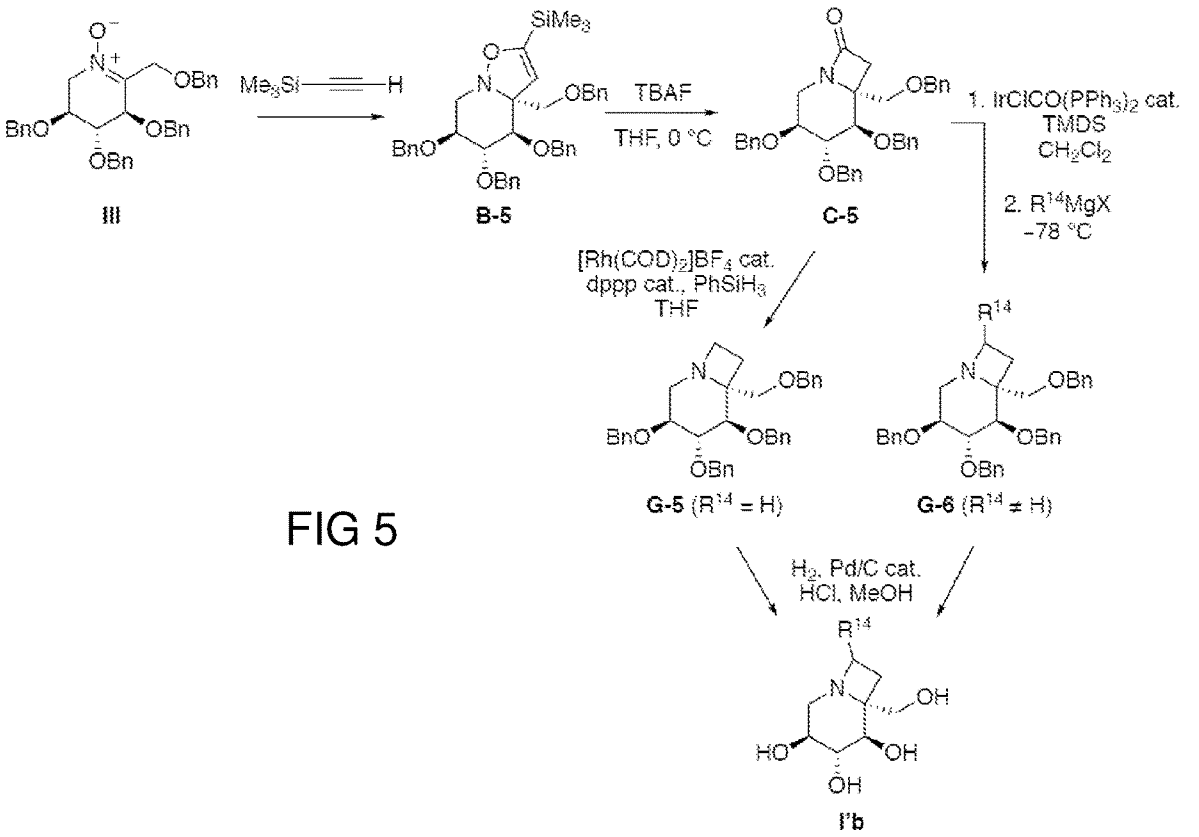
FIG. 5 shows first examples of general synthesis schemes (synthesis schemes 5) for preparing compounds of formula (I'b) according to the invention.
Figure 6:
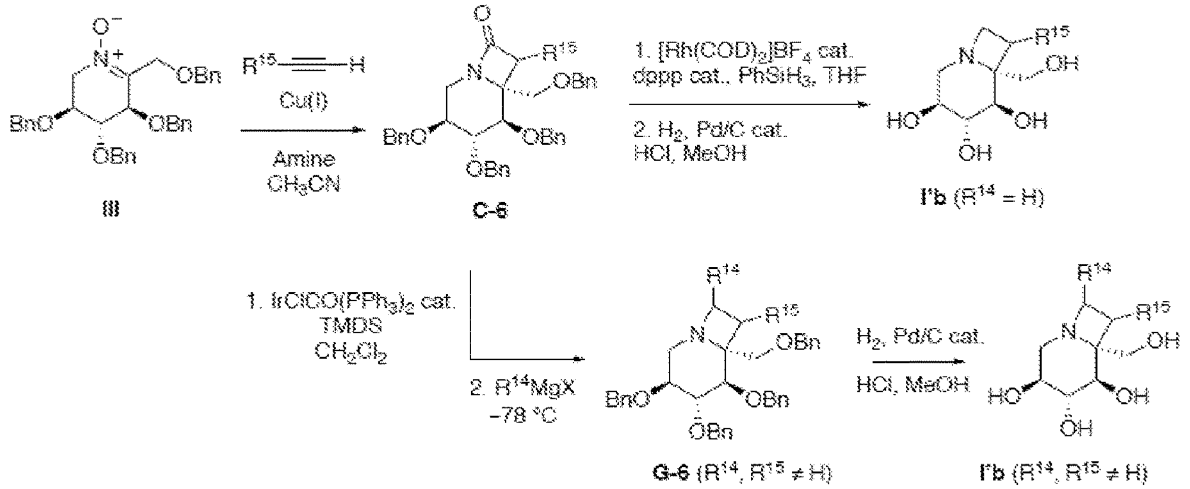
FIG. 6 shows a second example of general synthesis schemes (synthesis schemes 6) for preparing compounds of formula (I'b) according to the invention.

The synthesis method used for obtaining the compound complying with the general formula (I'b) as above falls under a general synthesis scheme 5 shown on FIG. 5.

Compound (IIh)

The compound of above formula (IIh) ((3S,4R,5R,6R)-6-(hydroxymethyl)-1-azabicyclo[4.2.0]octane-3,4,5-triol) is prepared in the following manner.

$[Rh(COD)_2]BF_4$ (2.5 mg, 0.006 mmol), 1,3-bis(diphenylphosphino)propane (2.7 mg, 0.006 mmol) and $PhSiH_3$ (25 μL, 0.20 mmol) were added to a solution of β-lactam C-5 (corresponding to the compound C-2 obtained as intermediate in synthesis method 2, as described in the protocol for preparing the compound (IId) above) (57.1 mg, 0.10 mmol) in distilled THF. The solution was stirred at 50° C. for 4 hours. After cooling, the reaction mixture was diluted with EtOAc and aqueous NaOH (1 M). The aqueous phase was extracted (three times) with EtOAc. The organic phases were washed with brine, dried over $MgSO_4$, and the solvents were evaporated under reduced pressure to give conidine G-5 (33.2 mg, 60%) after purification by chromatography. This compound (20.0 mg, 0.04 mmol) was debenzylated in accordance with the general procedure B to give the compound (IIh) (6.3 mg, 93%).

A pale yellow oil is obtained, with the following characteristics:

$[\alpha]^{20}_D$−5.17 (c 0.58, $CH_3OH$);

IR ν 3234, 2917, 1429, 1030 $cm^{-1}$;

$^1H$ NMR (500 MHz, $CD_3OD$) δ 2.18-2.26 (m, 1H), 2.55-2.63 (m, 1H), 2.89 (dd, J=5.9, 13.3 Hz, 1H), 3.21 (dd, J=5.1, 13.3 Hz, 1H), 3.62 (d, J=11.7 Hz, 1H), 3.69-3.80 (m, 5H), 3.99 (pst, J=6.5 Hz, 1H) ppm;

$^{13}C$ NMR (125 MHz, $CD_3OD$) δ 21.3 ($CH_2$), 51.4 ($CH_2$), 52.9 ($CH_2$), 65.5 ($CH_2$), 71.2 (CH), 72.7 (CH), 73.2 ($C_q$), 76.8 (CH) ppm;

HRMS ($ESI^+$) Calc. $C_8H_{16}NO_4$ $[M+H]^+$m/z=190.1074; Found m/z=190.1074.

General Protocol C—reducing alkylation of β-lactam C-5 leading to conidines of general formula (I'b)

A solution of β-lactam C-5 (1 equiv.) and of Vaska's catalyst (4% mol) in anhydrous dichloromethane under argon atmosphere is added to tetramethyldisiloxane (TMDS, 2 equiv.) at ambient temperature. The mixture is stirred for 45 minutes and then cooled to −78° C. Grignard reagent (2 equiv.) is added dropwise and then the mixture is stirred for 7-10 minutes at this same temperature before increasing to ambient temperature. It is next stirred for 21 hours. A saturated aqueous solution of $NH_4Cl$ is added and then the resulting mixture is diluted with $CH_2Cl_2$. The organic phase is separated and the aqueous phase is extracted twice with $CH_2Cl_2$. The organic phases are washed with brine, dried over $MgSO_4$ and evaporated under reduced pressure. The conidines of formula (I'b) thus formed are purified by chromatography over silica gel before being reduced and debenzylated in accordance with the general protocol B above.

Compound (IIz2)

The compound of above formula (IIz2) ((3S,4R,5R,6R,8R)-8-benzyl-6-(hydroxymethyl)-1-azabicyclo[4.2.0]octane-3,4,5-triol: 20.3 mg; 65% for 2 steps) was prepared in accordance with the general procedures C and B, from β-lactam C-5 (70.1 mg; 0.124 mmol) and 2M benzylmagnesium chloride in THF ($R^{14}$=Bn; 36.3 μL; 0.248 mmol).

A translucent lacquer is obtained, with the following characteristics:

$^1H$ NMR (500 MHz, $CD_3OD$) δ 7.39-7.20 (m, 5H), 4.45-4.34 (m, 1H), 3.95 (t, J=5.7 Hz, 1H), 3.80-3.74 (m, 2H), 3.70 (d, J=5.6 Hz, 1H), 3.56 (d, J=12.1 Hz, 1H), 3.21-3.12 (m, 2H), 3.00 (dd, J=13.6, 8.4 Hz, 1H), 2.94 (dd, J=13.1, 6.5 Hz, 1H), 2.60 (dd, J=11.9, 9.0 Hz, 1H), 2.32-2.20 (m, 1H) ppm;

$^{13}C$ NMR (125 MHz, $CD_3OD$) δ 137.1 ($^{Ar}Cq$), 130.1 ($^{Ar}CH$), 129.7 ($^{Ar}CH$), 128.0 ($^{Ar}CH$), 76.5 (CH), 71.5 (CH), 71.1 (CH), 65.7 (CH), 64.1 ($CH_2$), 51.4 ($CH_2$), 41.0 ($CH_2$), 27.3 ($CH_2$) ppm;

HRMS ($ESI^+$) Calc. C15H22$NO_4$ $[M+H]^+$: m/z=280.15433; Found m/z=280.15437.

Compound (IIz3)

The compound of above formula (IIz3) ((3S,4R,5R,6R,8R)-6-(hydroxymethyl)-8-methyl-1-azabicyclo[4.2.0]octane-3,4,5-triol: 8.5 mg; 46% for 2 steps) was prepared in accordance with the general procedures C and B, from β-lactam C-5 (192.6 mg; 0.342 mmol) and 3M methylmagnesium chloride in THF ($R^{14}$=Me; 228 μL; 0.683 mmol).

A yellowish solid is obtained, with the following characteristics:

[60]$^{20}_D$−22.9 (c 1.07, MeOH);

$^1H$ NMR (500 MHz, $CD_3OD$) δ 3.99 (t, J=6.7 Hz, 1H), 3.85-3.75 (m, 1H), 3.75-3.69 (m, 1H), 3.67 (d, J=7.6 Hz, 1H), 3.54 (d, J=11.2 Hz, 1H), 3.47 (d, J=11.2 Hz, 1H), 3.10 (dd, J=13.9, 5.5 Hz, 1H), 2.71 (dd, J=13.8, 4.0 Hz, 1H), 2.58 (dd, J=11.5, 8.9 Hz, 1H), 1.64 (dd, J=10.9, 8.0 Hz, 1H), 1.21 (d, J=6.1 Hz, 3H) ppm;

$^{13}C$ NMR (100 MHz, $CD_3OD$) δ 77.2 (CH), 74.7 (CH), 71.7 (CH), 68.3 (Cq), 67.4 ($CH_2$), 58.4 (CH), 52.4 ($CH_2$), 29.1 ($CH_2$), 22.0 ($CH_3$) ppm; HRMS ($ESI^+$) Calc. $C_9H_{18}NO_4$ $[M+H]^+$: m/z=204.12303; Found m/z=204.12232.

Compound (IIz4)

The compound of above formula (IIz4) ((3S,4R,5R,6R,8S)-8-cyclopentyl-6-(hydroxymethyl)-1-azabicyclo[4.2.0]octane-3,4,5-triol: 14.6 mg; 62% for 2 steps) was prepared in accordance with the general procedures C and B, from β-lactam C-5 (70.0 mg; 0.124 mmol) and 2M cyclopentylmagnesium chloride in ether ($R^{14}$=cPent; 36.4 μL; 0.248 mmol).

A yellowish solid is obtained, with the following characteristics:

$^1H$ NMR (500 MHz, $CD_3OD$) δ 3.98 (t, J=7.0 Hz, 1H), 3.76-3.63 (m, 2H), 3.58-3.36 (m, 3H), 3.10 (dd, J=14.5, 5.0 Hz, 1H), 2.76 (dd, J=14.5, 4.0 Hz, 1H), 2.50 (t, J=11.8 Hz, 1H), 2.06-1.95 (m, 1H), 1.89-1.76 (m, 1H), 1.74-1.47 (m, 6H), 1.36-1.22 (m, 1H), 1.15-1.00 (m, 1H) ppm;

$^{13}C$ NMR (125 MHz, $CD_3OD$) δ 77.7 (CH), 75.0 (CH), 71.9 (CH), 67.5 ($CH_2$), 67.2 (CH), 66.3 (Cq), 54.2 ($CH_2$), 48.9 (CH), 31.0 ($CH_2$), 29.1 ($CH_2$), 27.0 ($CH_2$), 26.4 ($CH_2$), 25.9 ($CH_2$) ppm;

HRMS ($ESI^+$) Calc. $C_{13}H_{24}NO_4$ $[M+H]^+$: m/z=258.16998; Found m/z=258.16987.

Compound (IIz5)

The compound of above formula (IIz5) ((3S,4R,5R,6R,8R)-6-(hydroxymethyl)-8-pentyl-1-azabicyclo[4.2.0]octane-3,4,5-triol: 19.1 mg; 45% for 2 steps) was prepared in accordance with the general procedures C and B, from β-lactam C-5 (70.0 mg; 0.124 mmol) and 2M pentylmagnesium chloride in THF ($R^{14}$=n-Pent; 33.6 μL; 0.248 mmol).

A yellow solid is obtained, with the following characteristics:

$[\alpha]^{20}_D$−31.1 (c 0.46, MeOH);

1H NMR (500 MHz, $CD_3OD$) δ 3.99 (t, J=7.0 Hz, 1H), 3.74-3.64 (m, 2H), 3.64-3.55 (m, 1H), 3.51 (d, J=11.1 Hz, 1H), 3.46 (d, J=11.1 Hz, 1H), 3.09 (dd, J=13.7, 5.4 Hz, 1H), 2.70 (dd, J=13.7, 4.0 Hz, 1H), 2.52 (dd, J=11.4, 8.9 Hz, 1H), 1.68-1.53 (m, 2H), 1.51-1.39 (m, 1H), 1.39-1.21 (m, 6H), 0.90 (t, J=6.7 Hz, 3H) ppm;

$^{13}C$ NMR (100 MHz, $CD_3OD$) δ 77.5 (CH), 75.2 (CH), 71.9 (CH), 67.8 ($CH_2$), 66.4 (Cq), 62.4 (CH), 53.8 ($CH_2$), 38.8 ($CH_2$), 33.0 ($CH_2$), 27.9 ($CH_2$), 26.5 ($CH_2$), 23.7 ($CH_2$), 14.3 ($CH_3$) ppm;

HRMS ($ESI^+$) Calc. $C_{13}H_{26}NO_4$ $[M+H]^+$: m/z=260.18563; Found m/z=260.18561.

A.6/ Synthesis Method 7

Figure 7:
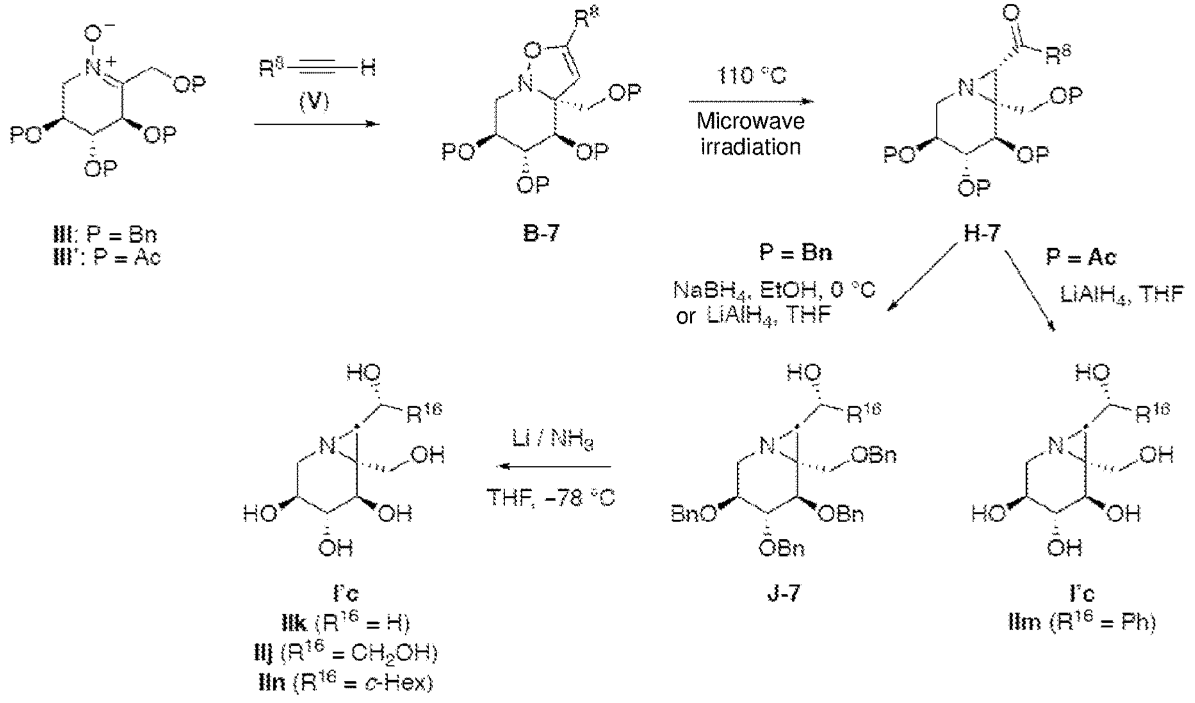
FIG. 7 shows an example of general synthesis schemes (synthesis schemes 7) for preparing compounds of formula (I'c) according to the invention.

The synthesis method used for obtaining the compounds complying with the general formula (I'c) below falls under the general synthesis scheme 7 shown on FIG. 7.

Compound (IIk)

The compound of formula (IIk) as above ((3S,4R,5R,6R,7S)-6,7-bis(hydroxymethyl)-1-azabicyclo[4.1.0]heptane-3,4,5-triol) is obtained in the following manner.

A mixture of nitrone (III) (P=Bn; 193 mg, 0.360 mmol) and of alkyne Vc ($R^8$=NBnTs; 308 mg, 1.079 mmol) in solution in $CH_2Cl_2$ (0.4 mL) was stirred at ambient temperature for 3 days, and then the reaction mixture was concentrated under reduced pressure. The residue (raw cycloadduct B-7c) was dissolved in ethanol (0.1M), transferred into a sealed tube, and heated at 110° C. (IR probe) under microwave irradiation for 15 minutes. After concentration under reduced pressure, the residue was purified by chromatography to give acylaziridine H-7c (P=Bn, $R^8$=NBnTs; 238 mg, 80% on 2 steps). A fraction of this compound (58 mg, 0.070 mmol) was dissolved in THF (1 mL), and then LiAlH4 (6 mg, 0.157 mmol) was added at 0° C. The mixture was stirred for 1.5 hours at ambient temperature. After adding water (0.1 mL) and a 10% aqueous solution of NaOH (0.1 mL), the reaction mixture was stirred at ambient temperature for 2 hours and then filtered over Celite®. The filtrate, concentrated under reduced pressure, was purified by chromatography to isolate the aziridine-alcohol J-7c (P=Bn, $R^{16}$=H; 34.2 mg, 86%). A solution of this aziridine-alcohol J-7c (28 mg, 0.067 mmol) in THF (2 mL) was added to a solution of lithium (54 mg, 7.78 mmol) in liquid ammonia (10 mL) at −78° C. The mixture was stirred for 45 minutes at −78° C., and then Milli-Q water (0.5 mL) and MeOH (2 mL) were added. After returning the solution to ambient temperature, the solvents were evaporated under reduced pressure. The residue was dissolved in Milli-Q water and neutralized with Amberlite® IR-120 (22.8 g) previously treated with 1M HCl (15 mL). The resin was introduced into a column, washed with water, and then the compound (IIk) was eluted with a 1M solution of aqueous $NH_4OH$. The solution obtained after evaporation of the solvents under reduced pressure was purified by chromatography to give the pure iminosugar (IIk) ($R^{16}$=H; 7 mg, 60%).

A white solid is obtained, with the following characteristics:

$[\alpha]^{20}_D$=+2.90 (c 0.34, $CH_3OH$);

IR ν 3409, 3010, 2926, 1084, 1032 $cm^{-1}$;

$^1H$ NMR (500 MHz, $CD_3OD$) δ 4.16 (d, J=7.9 Hz, 1H), 3.79 (d, J=11.6 Hz, 1H), 3.60-3.50 (m, 3H), 3.47-3.40 (m, 1H), 3.33-3.25 (m, 2H), 2.55 (dd, J=10.6, 12.4 Hz, 1H), 2.19 (dd, J=6.8, 5.3 Hz, 1H) ppm;

$^{13}C$ NMR (125 MHz, $CD_3OD$) δ 76.0 (CH), 73.2 (CH), 70.6 (CH), 63.2 ($CH_2$), 62.0 ($CH_2$), 57.0 ($CH_2$), 51.9 ($C_q$), 51.6 (CH) ppm;

HRMS ($ESI^+$) Calc. $C_8H_{16}NO_5$ $[M+H]^+$ m/z=206.1028; Found m/z=206.1028.

Compound (IIj)

The compound of above formula (IIj) ((3S,4R,5R,6R,7S)-7-((S)-1,2-dihydroxyethyl)-6-(hydroxymethyl)-1-azabicyclo[4.1.0]heptane-3,4,5-triol) is obtained as follows.

Acylaziridine H-7d (P=Bn, $R^8$=$CH_2$OAc; 33 mg, 0.052 mmol), obtained as described in the publication by Tangara et al., 2017, *Org. Lett.* 19: 4842-4845, was dissolved in THF (1 mL), and then LiAlH4 (38 mg, 0.165 mmol) was added at 0° C. and the mixture was stirred for 1 hour at ambient temperature. After adding water (0.1 mL) and a 10% aqueous solution of NaOH (0.1 mL), the reaction mixture was stirred at ambient temperature for 2 hours and then filtered over Celite®. The filtrate, concentrated under reduced pressure, was purified by chromatography to isolate a translucent oil J-7d ($R^{16}$=$CH_2OH$; 26 mg, 83%). A solution of this aziridine-alcohol J-7d (40 mg, 0.067 mmol) in THF (2 mL) was added to a solution of lithium (25 mg, 3.571 mmol) in liquid ammonia (10 mL) at −78° C. The mixture was stirred for 45 minutes at −78° C. and then Milli-Q water (0.5 mL) and MeOH (2 mL) were added. After returning the solution to ambient temperature, these solvents were evaporated under reduced pressure. The residue was dissolved in Milli-Q water and neutralized with Amberlite® IR-120 (8.5 g) previously treated with 1M HCl (5 mL). The resin was introduced into a column, washed with water, and then the compound (IIj) was eluted with a 1M solution of aqueous $NH_4OH$. The solid obtained after evaporation of the solvents under reduced pressure was purified by chromatography to give the pure iminosugar (IIj) ($R^{16}$=$CH_2OH$; 10.1 mg, 64%).

A white solid is obtained, with the following characteristics:

$[\alpha]^{20}_D$=+5.90 (c 0.34, $CH_3OH$);

IR: ν 3249, 2939, 2885, 1748, 1656, 1404, 1031, 995 $cm^{-1}$;

$^1H$ NMR (500 MHz, $CD_3OD$) δ 4.16 (d, J=8.0 Hz, 1H), 3.91 (d, J=11.6 Hz, 1H), 3.71 (dd, J=3.5, 11.4 Hz, 1H), 3.61 (dd, J=5.8, 11.4 Hz, 1H), 3.54-3.48 (m, 1H), 3.48-3.41 (m, 1H), 3.39 (d, J=11.6 Hz, 1H), 3.30-3.25 (m, 2H), 2.52 (dd, J=10.2, 12.2 Hz, 1H), 2.10 (d, J=8.7 Hz, 1H) ppm;

$^{13}C$ NMR (125 MHz, $CD_3OD$) δ 75.9 (CH), 73.1 (CH), 72.4 (CH), 70.7 (CH), 66.1 ($CH_2$), 63.8 ($CH_2$), 56.5 ($CH_2$), 52.0 ($C_q$), 51.2 (CH) ppm;

HRMS ($ESI^+$) Calc. $C_9H_{18}NO_6$ $[M+H]^+$m/z=236.1129; Found m/z=236.1124.

Compound (IIm)

The compound of above formula (IIm) (3S,4R,5R,6R,7S)-7-((S)-hydroxy(phenyl)methyl)-6-(hydroxymethyl)-1-azabicyclo[4.1.0]heptane-3,4,5-triol is obtained as follows.

The cycloadducts B-7e (P=Ac, $R^8$=Ph; 15.2 mg, 0.030 mmol, 4:1 mixture of diastereoisomers), obtained as described in the publication by Tangara et al., 2018, New J. Chem. 42: 16735-16743, were dissolved in dichloroethane (0.1M solution) in a sealed tube. The solution was heated at 110° C. (IR probe) under irradiation by microwave for 45 minutes (30+15). After evaporation of the solvent under reduced pressure, purification of the residue by chromatography made it possible to isolate the acylaziridines H-7e (P=Ac, $R^8$=Ph; 12 mg, 79%) in the form of a 9:1 mixture of two diastereoisomers. These acylaziridines (30 mg, 0.067 mmol) were dissolved in THF (1.2 mL), the solution was cooled to 0° C. and then LiAlH4 (5.6 mg, 0.147 mmol) was added. The reaction mixture was stirred at ambient temperature for 1.5 hours, and then water (0.1 mL) and a 10% aqueous solution of NaOH (0.1 mL) were added thereto. After stirring at ambient temperature for 1.5 hours, this mixture was filtered over Celite®, the filtrate being concentrated under reduced pressure, and the residue was purified by chromatography to provide the aziridinyl iminosugar (IIm) ($R^{16}$=Ph; 15 mg, 82%) in the form of a single diastereoisomer.

A colorless oil is obtained, with the following characteristics:

$[\alpha]^{20}_{D}$−4.1 (c 1.58, $CH_3OH$);

IR ν 3296, 2931, 1557, 1409, 1053, 697 $cm^{-1}$;

$^1H$ NMR (500 MHz, $CD_3OD$) δ 7.49-7.44 (m, 2H), 7.40-7.35 (m, 2H), 7.31-7.25 (m, 1H), 4.29 (d, J=8.7 Hz, 1H), 4.18 (d, J=7.9 Hz, 1H), 4.01 (d, J=11.6 Hz, 1H), 3.56 (d, J=11.6 Hz, 1H), 3.48-3.37 (m, 2H), 3.26 (dd, J=9.1, 8.0 Hz, 1H), 2.26-2.18 (m, 2H) ppm;

$^{13}C$ NMR (125 MHz, $CD_3OD$) δ 144.6 ($^{Ar}C_q$), 129.5 ($^{Ar}CH$), 128.6 ($^{Ar}CH$), 127.1 ($^{Ar}CH$), 75.8 (CH), 73.8 (CH), 73.1 (CH), 70.7 (CH), 63.6 ($CH_2$), 56.4 ($CH_2$), 56.0 (CH), 52.8 ($C_q$) ppm;

HRMS ($ESI^+$) Calc. $C_{14}H_{20}NO_5$ $[M+H]^+$: m/z=282.1341; Found m/z=282.1346.

Compound (IIn)

The compound of above formula (IIn) (3S,4R,5R,6R,7S)-7-((R)-cyclohexyl(hydroxy)methyl)-6-(hydroxymethyl)-1-azabicyclo[4.1.0]heptane-3,4,5-triol is obtained as follows.

Acylaziridine H-7f (P=Bn, $R^8$=c-Hex; 77 mg, 0.119 mmol), obtained as described in the publication by Tangara et al., 2017, Org. Lett. 19: 4842-4845, was dissolved in ethanol (1.4 mL), cooled to 0° C., and then $NaBH_4$ (13 mg, 0.342 mmol) was added. The mixture was stirred at the same temperature for 3.3 hours, and then water, a 10% aqueous solution of NaOH and $CH_2Cl_2$ were added. The aqueous phase was extracted (3 times) by $CH_2Cl_2$, the organic phases were collected, dried on $MgSO_4$ and concentrated under reduced pressure. The residue thus obtained was filtered on silica to isolate the aziridine-alcohol J-7f ($R^{16}$=c-Hex; 72 mg, 94%) in the form of an oil. A solution of this aziridine-alcohol J-7f (42 mg, 0.064 mmol) in THF (4 mL) was added to a solution of lithium (12 mg, 2.0 mmol) in liquid ammonia (10 mL) at −78° C. The reaction mixture was stirred for 45 minutes at −78° C., and then Milli-Q water (0.5 mL) and MeOH (2 mL) were added. After returning the solution to ambient temperature, the solvents were evaporated under reduced pressure. The residue was dissolved in Milli-Q water and neutralized with Amberlite® IR-120 (3.5 g) previously treated with 1M HCl (2 mL). The resin was introduced into a column, washed with water, and then the compound (IIn) was eluted with a 1M solution of aqueous $NH_4OH$. The solid obtained after evaporation of the solvents under reduced pressure was purified by chromatography to give the pure iminosugar (IIn) ($R^{16}$=c-Hex; 13 mg, 72%).

A white solid is obtained, with the following characteristics:

$[\alpha]^{20}_{D}$+2.8 (c 0.80, $CH_3OH$);

IR ν 3335, 2916, 2846, 1451, 1087, 1054, 1008, 660 $cm^{-1}$;

$^1H$ NMR (500 MHz, $CD_3OD$) δ 4.17 (d, J=7.8 Hz, 1H), 3.88 (d, J=11.7 Hz, 1H), 3.50-3.44 (m, 2H), 3.42 (d, J=11.7 Hz, 1H), 3.33-3.29 (m, 1H), 2.95 (dd, J=8.6, 6.6 Hz, 1H), 2.51 (dd, J=11.8, 9.0 Hz, 1H), 2.08 (d, J=8.7 Hz, 1H), 1.99-1.66 (m, 5H), 1.53-1.45 (m, 1H), 1.36-1.03 (m, 5H) ppm;

$^{13}C$ NMR(125 MHz, $CD_3OD$) δ 76.3 (CH), 76.0 (CH), 73.3 (CH), 70.8 (CH), 64.1 ($CH_2$), 56.0 ($CH_2$), 52.9 (CH), 51.1 ($C_q$), 45.3 (CH), 30.1 ($CH_2$), 29.7 ($CH_2$), 27.7 ($CH_2$), 27.4 ($CH_2$), 27.2 ($CH_2$) ppm;

HRMS ($ESI^+$) Calc. $C_{14}H_{26}NO_5$ $[M+H]^+$: m/z=288.1811; Found m/z=288.1810.

A.7/ Synthesis Method 8

Figure 8:
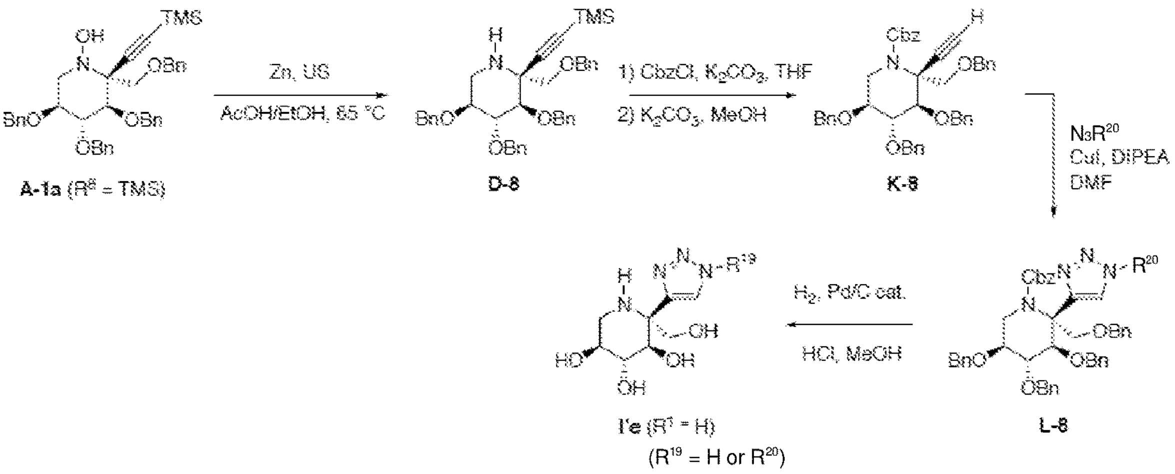
FIG. 8 shows an example of a general synthesis scheme (synthesis scheme 8) for preparing compounds of formula (I'e) according to the invention.

A synthesis method used for obtaining a compound complying with the general formula (I'e) below falls under the general synthesis scheme 8 shown on FIG. 8.

Compound (IIw1)

The compound of above formula (IIw1) ((2R,3R,4R,5S)-2-(hydroxymethyl)-2-(1H-1,2,3-triazol-4yl)piperidine-3,4,5-triol is prepared in the following manner. A solution of hydroxylamine of formula A-1a (240.0 mg; 0.377 mmol) and of zinc powder (247.0 mg; 3.77 mmol) in a 4:1 mixture EtOH/AcOH (5 mL) was stirred at 65° C. under ultrasound until the reaction was complete. The reaction mixture is filtered over Celite and then evaporated under reduced pressure. The raw product is redissolved in $CH_2Cl_2$ and then treated with aqueous 1M NaOH. The aqueous phase was extracted (three times) with $CH_2Cl_2$. The organic phases were washed with brine, dried over $MgSO_4$ and then evaporated under reduced pressure. Purification of the residue obtained by chromatography provided the corresponding piperidine D-8 (178.0 mg; 76%). A mixture of this piperidine D-8 (176.0 mg; 0.284 mmol), of benzyl chloroformiate (121 μL; 0.852 mmol) and of $K_2CO_3$ (157.0 mg; 1.14 mmol) in anhydrous THF (1.7 mL) was stirred at ambient temperature until the reaction was complete. Methanol (2 mL) was added and then the reaction mixture was stirred at ambient temperature until the reaction was complete. Purification of the residue obtained by chromatography provided the compound of formula K-8 (164.0 mg; 78% over 2 steps). Copper iodide (3.5 mg; 0.018 mmol) and DIPEA (108 μL; 0.618 mmol) were added to a solution of this same compound K-8 (46.8 mg; 0.062 mmol) and of benzyl azide (247 μL; 0.124 mmol) in DMF (1.5 mL) under inert atmosphere. The reaction mixture was stirred at ambient temperature until the reaction was complete. The raw product was diluted in ethyl acetate and washed several times with brine. The organic phase was dried over $MgSO_4$ and evaporated at reduced pressure. Purification of the residue obtained by chromatography provided the compound of formula L-8 (38.2 mg; 76%). This compound (32.1 mg; 0.039 mmol) was debenzylated in accordance with the general procedure B to give piperidine (IIw1) (11.0 mg; 100%).

A colorless lacquer is obtained, with the following characteristics:

$[\alpha]^{20}_{D}$−17.2 (c 1.09, $CH_3OH$);

1H NMR (500 MHz, $CD_3OD$) δ 7.90 (s, 1H), 3.80 (d, J=10.9 Hz, 1H), 3.69 (d, J=9.7 Hz, 1H), 3.59 (d, J=11.1 Hz, 1H), 3.52-3.45 (m, 1H), 3.27 (t, J=9.3 Hz, 1H), 2.99 (dd, J=12.6, 5.5 Hz, 1H), 2.54 (dd, J=12.3, 11.2 Hz, 1H) ppm;

$^{13}C$ NMR (125 MHz, $CD_3OD$) δ 144.5 (Cq), 131.0 (CH), 76.9 (CH), 74.5 (CH), 73.0 (CH), 68.1 ($CH_2$), 62.5 (Cq), 47.2 ($CH_2$) ppm;

HRMS ($ESI^+$) Calc. $C_8H_{15}N_4O_4$ $[M+H]^+$: m/z=231.10878; Found m/z=231.10861.

B/ Biological Evaluations

The following various biological activity tests are implemented on the compounds (IIa) to (IIn) described above.

B.1/ Inhibition of rhGAA Determined by Fluopol-ABPP

The inhibiting activity on recombinant human acid α-glucosidase (rhGAA) of the compounds is implemented using the Fluopol-ABPP method (Fluorescence Polarization Activity Based Protein Profiling) described in the publication of Lahav et al., 2017, J. Am. Chem. Soc. 139: 14192-14197. This technique, based on the competition between an inhibitor and a fluorescent probe capable of binding covalently to the active site of an enzyme, makes it possible to measure the affinity of this inhibitor for the active site of the rhGAA enzyme used for these experiments by the laboratory of Professors Herman S. Overkleeft and Johanes M. F. G. Aerts, Leiden Institute of Chemistry, Leiden University (NL), is the enzyme marketed under the name Myozyme®. The median inhibiting concentrations ($IC_{50}$) are determined in the Mcllvaine buffer (citrate-phosphate) 150 mM at pH 5.0, in the presence of 0.1% bovine gamma-globulin (p/v) and 0.5 mg/mL of Chaps detergent (Sigma) in 96-well plates (Griener). The rhGAA enzyme (10 μg/mL) is pre-incubated with solutions of inhibitor (containing 2.5% DMSO that was used to prepare the mother solutions of the compounds) at various concentrations [I] in the buffer, for 45 minutes at 37° C. The tetraaminomethylrhodamine (TAMRA) fluorescent probe in solution (25 nM) in the buffer is next added to the mixture. After 4 hours, the samples are irradiated with a polarized light (λ=530 nm) and the fluorescence emitted (λ=580 nm) is measured by means of an Infinite® M1000Pro (Tecan) spectrofluorimeter. For each concentration of inhibitor, the percentage of inhibition of the enzyme is determined by the formula:

$$\%\,\text{Inhibition} = [F_{measured} - F_{control1})/F_{control2}) \times 100$$

where $F_{measured}$ corresponds to the fluorescence measured in the presence of the iminosugars; $F_{control1}$ corresponds to the fluorescence measured in the presence of a powerful inhibitor of human acid α-glucosidase acid serving as a positive control (100% inhibition), CF 022 ((1S,2R,3S,4R,5R,6R)-2,3,4-trihydroxy-5-(hydroxymethyl)-7-(8-azidooctyl)-7-aza-bicyclo[4.1.0]heptane), and $F_{control2}$ represents the fluorescence of the probe measured in the absence of the inhibitor (0% inhibition).

The $IC_{50}$ values are calculated by a non-linear regression of the % inhibition as a function of the concentration [I] by means of the GraphPad Prism 6.0 software. The results are a mean of three identical experiments (triplicates).

B.2/ Inhibition of rhGAA Determined by Measuring the Residual Activity in the Presence of an Inhibitor in Vitro In a complementary way, the activity of inhibition of recombinant human acid α-glucosidase (rhGAA) of the compounds was evaluated by the team of Professor Marco Moracci, Department of Biology, University of Naples Federico II (IT), using the method described in the publication of Porto et al., 2012, Molecular Therapy 20: 2201-2211. The rhGAA enzyme sold under the name Myozyme® used comes from residues of perfusions of the recombinant enzyme used for treating, by enzyme therapy, the patients with Pompe disease in the Department of Translational Medical Sciences, University of Naples Federico II (IT). The compounds are solubilized at various concentrations in a 100 mM sodium acetate buffer, pH 4.0, as well as the 4-nitrophenyl-α-D-glucopyranoside substrate (20 mM). After 2 minutes of equilibration of the temperature at 37° C., the rhGAA enzyme in solution in the same buffer is added (total volume: 200 μL). After 2 minutes of reaction at 37° C., a 1M solution of sodium carbonate (800 μL), pH 11.0, is added and the mixture is cooled in ice. The absorbance of the solution is measured at 420 nm at ambient temperature. The spontaneous hydrolysis of the substrate is subtracted by measuring the absorbance of controls (blanks) without enzyme. The results given are the mean of at least two identical experiments. The data are processed and analyzed using Prism 5.0 software (GraphPad).

B.3/ Determination of the Thermal Stabilization of rhGAA

The stabilization of rhGAA in the presence of the compounds is determined in accordance with the method described in the publication of Niesen et al., 2007, Nat. Protoc. 2: 2212-2221. The rhGAA enzyme (2.5 μg, 0.1 mg/mL) is incubated in the absence and in the presence of each compound (at a concentration [I]=100 μM), of SYPRO® orange dye (Life Technologies), and of sodium phosphate buffer (25 mM) and of NaCl (150 mM), pH 7.4 or of sodium acetate buffer (25 mmol) and of NaCl (150 mM), pH 4.0. The thermal stability of the enzyme in these various conditions is evaluated by DSF (differential scanning fluorimetry) by varying the temperature by 1° C./min over an interval of 25 to 95° C., and measuring the fluorescence of the SYPRO® orange dye every minute by means of a Real-Time Cycler spectrofluorimeter (Biorad). The relative fluorescence is determined by comparing each fluorescence value measured with that of the maximum fluorescence value of the SYPRO® orange dye for each scan. The results are a mean of three identical experiments (triplicates).

B.4/ Evaluation of the Inhibition of Other Enzymes of Human Origin

The selectivity of the compounds was evaluated in the laboratory of Professors Herman S. Overkleeft and Johanes M. F. G. Aerts, Leiden Institute of Chemistry, Leiden University (NL). The enzymes used for determining the selectivity of inhibition of the compounds with respect to various human enzymes are the α-glucosidase II of the endoplasmic reticulum (GANAB), recombinant human lysosomal β-glucocerebrosidase (GBA1), human non-lysosomal β-glucosylceramidase (GBA2) and β-glucosylceramide synthase (GCS). The inhibiting activity of the compounds on these various enzymes is determined as described in the publication by Artola et al., 2017, ACS Cent. Sci. 3: 784-793. The enzyme GBA1 sold under the name Cerezyme® and the enzyme rhGAA sold under the name Myozyme® are used. The human GANAB enzyme used for this study is that of fibroblasts of patients suffering from Pompe disease diagnosed as lacking active GAA and voluntary donors. These fibroblasts were cultivated on an HAMF12-DMEM medium (Sigma) supplemented by 10% (v/v) FCS (fetal calf serum). The GBA2 enzyme was overexpressed in HEK298T cells cultivated on a DMEM medium enriched with glucose (Gibco) supplemented by 10% NBS (newborn bovine serum) and 100 units/mL of penicillin/streptomycin (Gibco) and 5% $CO_2$ at 37° C. The activity of the compounds on human β-glucosylceramide synthase (GCS) is evaluated in situ on cells of the RAW 264.7 type cultivated on an RPMI medium (Gibco) supplemented by 10% FCS, 1 mM of glutamax, 100 units/mL of penicillin/streptomycin (Gibco) and 5% $CO_2$ at 37° C.

The $IC_{50}$ values for the GANAB, GBA2 and GCS enzymes are determined from cell lysates prepared in a buffer (20 mM hepes, 2 mM DTT, 0.25 M sucrose, 1 mM $MgCl_2$, 2.5 U/mL benzonase) at pH 7.0, and placed on ice for 30 minutes. These cell lysates are homogenized using a SilentCrusher grinder (Heidolph®), and then subjected to ultracentrifugation at 32,000 rpm for 30 minutes at 4° C. The total protein concentration is determined in accordance with the Bradford method (Bradford, 1976, Anal. Biochem. 72: 248-254), using a Bradford BioRad Quick Start® kit (Pierce) and BSA (Sigma). The lysates are next aliquoted and stored at −80° C. before use.

The $IC_{50}$ values for the GANAB enzyme are determined on cell lysates of fibroblasts of patients suffering from Pompe disease, using as a buffer the Mcllvaine 150 mM, pH 7.0, 0.1% bovine serum albumin (BSA) (p/v), a substrate (4-methyl-umbelliferone-α-D-glucopyranoside) concentration of 2.4 mM and an incubation time of 2 hours.

The $IC_{50}$ values for the GBA1 enzyme are determined using as buffer the McIlvaine 150 mM, pH 5.2, 0.2% taurocholate (p/v), 0.1% Triton X-100 (v/v), 0.1% bovine serum albumin (BSA) (p/v), an enzyme concentration of 0.7 nM, a substrate (4-methyl-umbelliferone-β-Dglucopyranoside) concentration of 3.0 mM and an incubation time of 30 minutes.

The residual activity of GBA2 in the presence of the compounds is determined after pre-incubation for 30 minutes of the homogenates of HEK298T cells over-expressing GBA2 with an inhibitor of GBA1, conduritol β-epoxide (Sigma), at a concentration of 1 mM. The $IC_{50}$ values are determined on cell lysates, using as a buffer the McIlvaine 150 mM, pH 5.8, 0.1% bovine serum albumin (BSA) (p/v), a substrate (4-methyl-umbelliferone-β-D-glucopyranoside) concentration of 3.0 mM and an incubation time of 1 hour.

The residual activity of GCS in the presence of the compounds is determined after pre-incubation for 1 hour of the homogenates of RAW 264.7 cells with an inhibitor of GBA1, conduritol β-epoxide (Sigma), at a concentration of 300 μM.

The $I_{50}$ values for the GCS enzyme are determined in situ in the cell culture medium at pH 7.0 using 1 μM of NBD-ceramide (N-[12-[(7-nitro-2-1,3-benzoxadiazol-4-yl) amino]dodecanoyl]-D-erythro-sphingosine) as substrate, as described in the aforementioned publication of Lahav et al.

The results obtained for all these tests are set out in tables 1 and 2 below. In these tables, by way of comparison, the values obtained for the compounds of the prior art DNJ and NB-DNJ, as described in the literature, are also indicated. In these tables: [a] indicates Porto et al., 2012, Mol. Ther. 20: 2201-2211; [b] indicates Bruckmann et al., 2012, ChemMedChem 7: 1943-1953; [c] indicates Flanagan et al., 2009, Human Mut. 30: 1683-1692; [d] indicates D'Alonzo et al., 2017, J. Med. Chem. 60: 9462-9469; * indicates ΔTm measured at [compound]=10 times the value of $K_i$; [e] indicates Asano et al., 1995, J. Med. Chem. 38: 2349-56; [f] indicates Wennekes et al., 2010, J. Med. Chem. 53: 689-698.

TABLE 1

| Compound | rhGAA (Fluopol-ABPP) $IC_{50}$ (μM) | rhGAA (residual activity) $IC_{50}$ (μM) | rhGAA ΔTm at pH 4.0 (° C.) | rhGAA ΔTm at pH 7.4 (° C.) |
|---|---|---|---|---|
| (IIa) | 0.42 | 341 | 8.1 | 12.7 |
| (IIb) | 0.39 | 104 (Ki = 13 μM) | 7.8 | 11.5 |
| (IIc) | 0.22 | 37.2 ($K_i$ = 7.6 μM) | 11.8 | 13.0 |
| (IId) | 0.15 | 182 ($K_i$ = 18.9 μM) | 9.4 | 10.7 |
| (IIf) | 0.87 | 297 | 6.4 | 11.8 |
| (IIg) | 0.46 | 387 | 6.7 | 14.4 |
| (IIh) | 9.7 | — | — | — |
| (IIj) | 15.2 | — | — | — |
| (IIk) | 11.6 | — | — | — |
| (IIm) | 45.0 | — | — | — |
| (IIn) | 24.6 | — | — | — |
| (IIx1) | — | 40.3 | — | 16.5 |
| (IIb7) | — | 31.6 | — | 16.8 |
| (IIb3) | — | 29.6 ($K_i$ = 10.8 μM) | — | 16.9 |
| (IIc1) | — | 32.9 ($K_i$ = 13.0 μM) | — | 15.0 |
| (IIr) | — | 29.5 ($K_i$ = 20.0 μM) | — | 14.5 |

TABLE 1-continued

| Compound | rhGAA (Fluopol-ABPP) $IC_{50}$ (μM) | rhGAA (residual activity) $IC_{50}$ (μM) | rhGAA ΔTm at pH 4.0 (° C.) | rhGAA ΔTm at pH 7.4 (° C.) |
|---|---|---|---|---|
| (IIb1) | — | 49.1 ($K_i$ = 6.4 μM) | — | 6.2 |
| DNJ | 0.41 | $K_i$ = 3.4 μM[a] | 2.7 (pH 4.3)*[b] | 15[c] |
| NB-DNJ | — | $K_i$ = 3.1 μM[b] | 6.2 (pH 4.3)*[b] | 12[d] |

TABLE 2

| Compound | GANAB $IC_{50}$ (μM) | GBA1 $IC_{50}$ (μM) | GBA2 $IC_{50}$ (μM) | GCS $IC_{50}$ (μM) |
|---|---|---|---|---|
| (IIa) | >100 | >1000 | >1000 | >50 |
| (IIb) | >100 | >1000 | >1000 | >50 |
| (IIc) | >100 | >1000 | >1000 | >50 |
| (IId) | >100 | >1000 | >1000 | >50 |
| (IIf) | >100 | >1000 | >1000 | >50 |
| (IIg) | >100 | >1000 | >1000 | >50 |
| DNJ | 4.6[e] | 250[f] | 21[f] | >100[f] |
| NB-DNJ | 15[e] | 400[f] | 0.23[f] | 50[f] |

All these results demonstrate a selectivity of the compounds used in accordance with the invention for human acid α-glucosidase, compared with the other human enzymes tested. This selectivity is much greater than that of the molecules proposed by the prior art DNJ and NB-DNJ. The compounds used in accordance with the invention furthermore have an important effect of stabilization of rhGAA, comparable to that of DNJ and NB-DNJ.

Furthermore, the compounds (IIb7), (IIb3), (IIc1), (IIr) and (Ic), complying with the general formula (I"a), as well as the compound (IIx1), have performances superior to those of the other compounds according to the invention.

The invention claimed is:

1. A method of treating Pompe disease in subject, comprising administering to said subject a therapeutically-effective amount of a compound of general formula (I), or one of the pharmaceutically acceptable salts thereof:

(I)

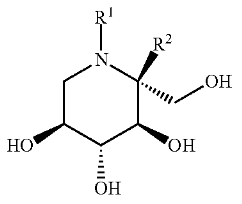

wherein $R^1$ represents a hydrogen atom or a linear, branched or cyclic hydrocarbon radical, saturated or unsaturated, aromatic or not, optionally substituted, optionally comprising one or more heteroatoms or one or more groups including at least one heteroatom, and optionally comprising a single ring or a plurality of rings optionally fused, and $R^2$ represents a $-(CHR^7)-SO_2-Ar^1$ group wherein $Ar^1$ represents an aryl or heteroaryl radical, optionally substituted, and $R^7$ represents a hydrogen atom or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, a triazole group, optionally substituted, or a $—(CH_2)_2—R^8$ group, wherein $R^8$ represents:

a C3 cycloalkyl group, optionally substituted, a linear, branched or cyclic hydrocarbon radical, saturated or unsaturated, aromatic or not, optionally substituted, comprising from 4 to 18 carbon atoms, optionally comprising one or more heteroatoms or one or more groups including at least one heteroatom and optionally comprising a single ring or a plurality of rings optionally fused, a $—(CH_2)_a—OH$ group, wherein a is an integer between 0 and 18, a $—(CH_2)_b—Ar^2$ group wherein $Ar^2$ represents an aryl or heteroaryl radical, optionally substituted, optionally comprising one or more heteroatoms and/or one or more groups including at least one heteroatom and optionally comprising a single ring or a plurality of rings optionally fused and b is an integer between 0 and 18, a $—(CH_2)_c—Si(R^9)_3$ group wherein $R^9$ represents a hydroxyl radical, a C1-C4 alkyl radical, a C1-C4 alkoxyl radical or a phenyl radical and c is an integer between 0 and 18, or a $—(CH_2)_d—Z—R^{10}$ group wherein Z is a heteroatom selected from the group consisting of oxygen, nitrogen and sulfur, $R^{10}$ represents a C1-C18 alkyl, cycloalkyl, alkylaryl, aryl or acyl radical, said radical optionally being interrupted or substituted by one or more heteroatoms and/or one or more groups including at least one heteroatom, and d is an integer between 0 and 18;

or $R^1$ and $R^2$ form together, with the atoms of the piperidine ring to which each is attached, a 4-membered heterocycle fused with the piperidine ring, optionally substituted by one or more radicals, which may be identical or different, each selected from the group consisting of a hydroxyl group, an amino group or a linear, branched or cyclic carbon radical, saturated or unsaturated, aromatic or not, optionally substituted, optionally comprising one or more heteroatoms and/or one or more groups including at least one heteroatom and optionally comprising a single ring or a plurality of rings optionally fused, or $R^1$ and $R^2$ form together, with the atoms of the piperidine ring to which each is attached, a 3-membered heterocycle fused with the piperidine ring, optionally substituted by a $—X—R^5$ group, wherein X represents a $—C(=O)—$ or $—CH(OR^6)—$ radical wherein $R^6$ represents a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, and $R^5$ represents a hydrogen atom, an amino group or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused;

or a $—CH(OH)—$ radical and $R^5$ represents a hydrogen atom or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, $R^5$ not representing an n-propyl radical, a cyclohexyl radical or a phenyl radical.

2. The method of claim 1, wherein, in the general formula (I), $R^1$ represents a C1-C18 linear, branched and/or cyclic alkyl group, optionally interrupted and/or substituted by one or more heteroatoms and one or more groups including at least one heteroatom.

3. The method of claim 1, wherein said compound has the general formula (I'a):

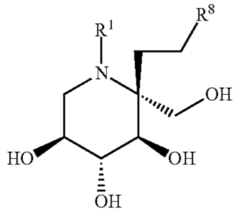

(I'a)

wherein:

$R^1$ represents a hydrogen atom or C1-C18 linear, branched and/or cyclic alkyl group, optionally interrupted and/or substituted by one or more heteroatoms and/or one or more groups including at least one heteroatom, $R^8$ represents: a pentyl, hexyl, cyclohexyl, adamantyl, alkylcycloalkyl, alkylaryl or aryl radical, said radical optionally being interrupted and/or substituted by one or more heteroatoms and/or one or more groups including at least one heteroatom; a hydroxyl group; a $—Si(R^{12})_3$ group wherein $R^{12}$ represents a hydroxyl radical, a C1-C4 alkyl radical, a C1-C4 alkoxyl radical or a phenyl radical; a $—(CH_2)_f—Y—R^{13}$ group wherein f is an integer between 0 and 6, Y is a heteroatom selected from the group consisting of oxygen, nitrogen and sulfur and $R^{13}$ represents a C1-C18 alkyl radical or a C1-C18 aryl or heteroaryl radical; a $—(CH_2)_g—CO—R^{13}$ group wherein g is an integer between 0 and 6; or a $—(CH_2)_h—SO_e—R^{13}$ group wherein h is an integer between 0 and 6 and e is equal to 1 or 2.

4. The method of claim 1, wherein said compound has the general formula (I"a):

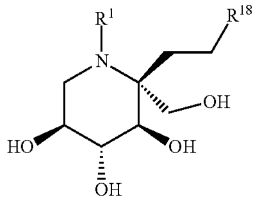

(I"a)

wherein:

$R^1$ represents a hydrogen atom or a C1-C18 linear, branched and/or cyclic alkyl group, optionally interrupted and/or substituted by one or more heteroatoms and/or one or more groups including at least one heteroatom, $R^{18}$ represents a linear, branched and/or cyclic hydrocarbon radical, saturated or unsaturated, aromatic or not, optionally substituted, comprising 4 to 18 carbon atoms, optionally comprising one or more heteroatoms and/or one or more groups including at least one heteroatom and optionally comprising a single ring or a plurality of rings optionally fused.

5. The method of claim 1, wherein said compound has the general formula (I'b):

(I'b)

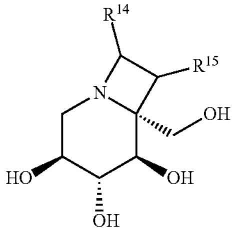

wherein $R^{14}$ represents a hydrogen atom, a carbonyl radical or a C1-C18 alkyl, alkenyl, alkynyl, alkylaryl or aryl radical, said radical optionally being interrupted and/or substituted by one or more heteroatoms and/or one or more groups including at least one heteroatom, and $R^{15}$ represents a hydrogen atom, a hydroxyl radical, an amino radical, or a C1-C18 alkyl, alkenyl or aryl radical, optionally interrupted and/or substituted by one or more heteroatoms and/or one or more groups including at least one heteroatom.

6. A pharmaceutical composition containing a compound of general (I) or one of the pharmaceutically acceptable salts thereof in a pharmaceutically acceptable vehicle:

(I)

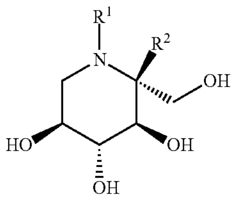

wherein $R^1$ represents a hydrogen atom or a linear, branched or cyclic hydrocarbon radical, saturated or unsaturated, aromatic or not, optionally substituted, optionally comprising one or more heteroatoms or one or more groups including at least one heteroatom, and optionally comprising a single ring or a plurality of rings optionally fused, $R^2$ represents a —$(CHR^7)$—$SO_2$—$Ar^1$ group wherein $Ar^1$ represents an aryl or heteroaryl radical, optionally substituted, and $R^7$ represents a hydrogen atom or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, a triazole group, optionally substituted, or a —$(CH_2)_2$—$R^8$ group, wherein $R^8$ represents:

a C3 cycloalkyl group, optionally substituted, a linear, branched or cyclic hydrocarbon radical, saturated or unsaturated, aromatic or not, optionally substituted, comprising from 4 to 18 carbon atoms, optionally comprising one or more heteroatoms or one or more groups including at least one heteroatom and optionally comprising a single ring or a plurality of rings optionally fused, a —$(CH_2)_a$—OH group, wherein a is an integer between 0 and 18, a —$(CH_2)_b$—$Ar^2$ group wherein $Ar^2$ represents an aryl or heteroaryl radical, optionally substituted, optionally comprising one or more heteroatoms and/or one or more groups including at least one heteroatom and optionally comprising a single ring or a plurality of rings optionally fused and b is an integer between 0 and 18, a —$(CH_2)_c$—$Si(R^9)_3$ group wherein $R^9$ represents a hydroxyl radical, a C1-C4 alkyl radical, a C1-C4 alkoxyl radical or a phenyl radical and c is an integer between 0 and 18, or a —$(CH_2)_d$—Z—$R^{10}$ group wherein Z is a heteroatom selected from the group consisting of oxygen, nitrogen and sulfur, $R^{10}$ represents a C1-C18 alkyl, cycloalkyl, alkylaryl, aryl or acyl radical, said radical optionally being interrupted or substituted by one or more heteroatoms and/or one or more groups including at least one heteroatom, and d is an integer between 0 and 18;

or $R^1$ and $R^2$ form together, with the atoms of the piperidine ring to which each is attached, a 4-membered heterocycle fused with the piperidine ring, optionally substituted by one or more radicals, which may be identical or different, each selected from the group consisting of a hydroxyl group, an amino group or a linear, branched or cyclic carbon radical, saturated or unsaturated, aromatic or not, optionally substituted, optionally comprising one or more heteroatoms and/or one or more groups including at least one heteroatom and optionally comprising a single ring or a plurality of rings optionally fused, or $R^1$ and $R^2$ form together, with the atoms of the piperidine ring to which each is attached, a 3-membered heterocycle fused with the piperidine ring, optionally substituted by a —X—$R^5$ group, wherein X represents:

a —C(=O)—or —$CH(OR^6)$— radical wherein $R^6$ represents a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, and $R^5$ represents a hydrogen atom, an amino group or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused;

or a —CH(OH)— radical and $R^5$ represents a hydrogen atom or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, $R^5$ not representing an n-propyl radical, a cyclohexyl radical or a phenyl radical.

7. The pharmaceutical composition of claim 6, which is in a form suitable for oral administration.

8. A compound of general formula (I):

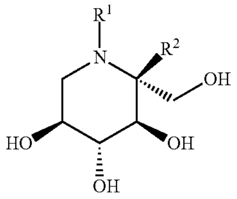

(I)

wherein $R^1$ represents a hydrogen atom or a linear, branched or cyclic hydrocarbon radical, saturated or unsaturated, aromatic or not, optionally substituted, optionally comprising one or more heteroatoms or one or more groups including at least one heteroatom, and optionally comprising a single ring or a plurality of rings optionally fused, $R^2$ represents a —$(CHR^7)$—$SO_2$—$Ar^1$ group wherein $Ar^1$ represents an aryl or heteroaryl radical, optionally substituted, and $R^7$ represents a hydrogen atom or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, a triazole group, optionally substituted, or a —$(CH_2)_2$—$R^8$ group, wherein $R^8$ represents:

a C3 cycloalkyl group, optionally substituted, a linear, branched or cyclic hydrocarbon radical, saturated or unsaturated, aromatic or not, optionally substituted, comprising from 4 to 18 carbon atoms, optionally comprising one or more heteroatoms or one or more groups including at least one heteroatom and optionally comprising a single ring or a plurality of rings optionally fused, a —$(CH_2)_a$—OH group, wherein a is an integer between 0 and 18, a —$(CH_2)_b$—$Ar^2$ group wherein $Ar^2$ represents an aryl or heteroaryl radical, optionally substituted, optionally comprising one or more heteroatoms and/or one or more groups including at least one heteroatom and optionally comprising a single ring or a plurality of rings optionally fused and b is an integer between 0 and 18, a —$(CH_2)$ c-Si $(R^9)_3$ group wherein $R^9$ represents a hydroxyl radical, a C1-C4 alkyl radical, a C1-C4 alkoxyl radical or a phenyl radical and c is an integer between 0 and 18, or a —$(CH_2)_d$—Z—$R^{10}$ group wherein Z is a heteroatom selected from the group consisting of oxygen, nitrogen and sulfur, $R^{10}$ represents a C1-C18 alkyl, cycloalkyl, alkylaryl, aryl or acyl radical, said radical optionally being interrupted or substituted by one or more heteroatoms and/or one or more groups including at least one heteroatom, and d is an integer between 0 and 18;

or $R^1$ and $R^2$ form together, with the atoms of the piperidine ring to which each is attached, a 4-membered heterocycle fused with the piperidine ring, optionally substituted by one or more radicals, which may be identical or different, each selected from the group consisting of a hydroxyl group, an amino group or a linear, branched or cyclic carbon radical, saturated or unsaturated, aromatic or not, optionally substituted, optionally comprising one or more heteroatoms and/or one or more groups including at least one heteroatom and optionally comprising a single ring or a plurality of rings optionally fused, or $R^1$ and $R^2$ form together, with the atoms of the piperidine ring to which each is attached, a 3-membered heterocycle fused with the piperidine ring, optionally substituted by a —X—$R^5$ group, wherein X represents:

a —C(=O)— or —CH($OR^6$)— radical wherein $R^6$ represents a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, and $R^5$ represents a hydrogen atom, an amino group or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused;

or a —CH(OH)— radical and $R^5$ represents a hydrogen atom or a linear, branched or cyclic hydrocarbon radical, saturated or unsaturated, aromatic or not, optionally substituted, optionally comprising one or more heteroatoms or one or more groups including at least one heteroatom and optionally comprising a single ring or a plurality of rings optionally fused, $R^5$ not representing an n-propyl radical, a cyclohexyl radical or a phenyl radical.

9. The compound of claim 8, of general formula (I'a):

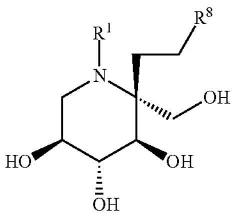

(I'a)

wherein $R^1$ represents a hydrogen atom or a C1-C18 linear, branched and/or cyclic alkyl group, optionally interrupted and/or substituted by one or more heteroatoms and/or one or more groups including at least one heteroatom, $R^8$ represents: a hydroxyl group; a pentyl, hexyl, cyclohexyl, adamantyl, alkylcycloalkyl, alkylaryl or aryl radical, said radical optionally being interrupted and/or substituted by one or more heteroatoms and/or one or more groups including at least one heteroatom; a —$Si(R^{12})_3$ group wherein $R^{12}$ represents a hydroxyl radical, a C1-C4 alkyl radical, a C1-C4 alkoxyl radical or a phenyl radical; a —$(CH_2)_f$—Y—$R^{13}$ group wherein f is an integer between 0 and 6, Y is a heteroatom selected from the group consisting of oxygen, nitrogen and sulfur and $R^{13}$ represents a C1-C18 alkyl radical or a C1-C18 aryl or heteroaryl radical; a —$(CH_2)_g$—CO—$R^{13}$ group wherein g is an integer between 0 and 6; or a —$(CH_2)_h$—$SO_e$—$R^{13}$ group wherein h is an integer between 0 and 6 and e is equal to 1 or 2.

10. The compound of claim 8, of general formula (I"a):

(I"a)

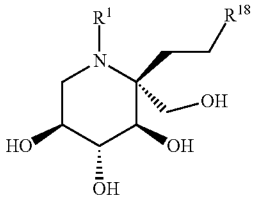

wherein:

$R^1$ represents a hydrogen atom or a C1-C18 linear, branched and/or cyclic alkyl group, optionally interrupted and/or substituted by one or more heteroatoms and/or one or more groups including at least one heteroatom, $R^{18}$ represents a linear, branched and/or cyclic hydrocarbon radical, saturated or unsaturated, aromatic or not, optionally substituted, comprising from 4 to 18 carbon atoms, optionally comprising one or more heteroatoms and/or one or more groups including at least one heteroatom and optionally comprising a single ring or a plurality of rings optionally fused.

11. The compound of claim 8, of formula (I'b):

(I'b)

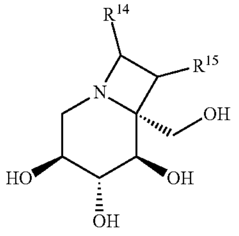

wherein $R^{14}$ represents a hydrogen atom, a carbonyl radical or a C1-C18 alkyl, alkenyl, alkynyl, alkylaryl or aryl radical, said radical optionally being interrupted and/or substituted by one or more heteroatoms and/or one or more groups including at least one heteroatom, and $R^{15}$ represents a hydrogen atom, a hydroxyl radical, an amino radical or a C1-C18 alkyl, alkenyl or aryl radical, optionally interrupted and/or substituted by one or more heteroatoms and/or one or more groups including at least one heteroatom.

12. The compound of claim 8, of formula (I'c):

(I'c)

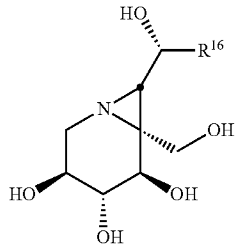

wherein $R^{16}$ represents a hydrogen atom or a C1-C18 alkyl radical, said radical optionally being interrupted and/or substituted by one or more heteroatoms and/or one or more groups including at least one heteroatom, $R^{16}$ not representing an n-propyl radical, a cyclohexyl radical or a phenyl radical.

13. A method for preparing the compound of claim 8, comprising successive steps of:

a/reacting a compound of general formula (III) or (IV) of formulae:

(III)

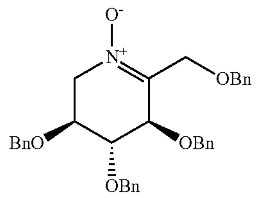

(IV)

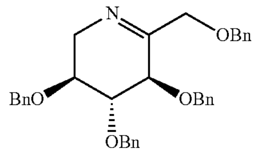

wherein Bn represents a benzyl radical, with a compound of general formula (V):

(V)

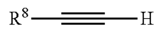

wherein $R^8$ is as defined in claim 8, $R^8$ however not representing a hydroxyl group, in the presence of an organometallic compound, b/optionally, reduction of the hydroxylamine function into amine, c/optionally, alkylation of the nitrogen atom of the piperidine ring, d/and hydrogenolysis of the product obtained at the end of step a/, where applicable of step b/or of step c/.

14. The compound of claim 8, having the formula (IIc):
(IIc)
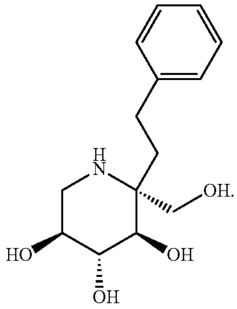
* * * * *